US00RE35948E

United States Patent [19]

Hider et al.

[11] E Patent Number: Re. 35,948

[45] Reissued Date of Patent: Nov. 3, 1998

[54] PHARMACEUTICAL COMPOSITIONS

[75] Inventors: Robert C. Hider, Clacton; George Kontoghiorghes; Jack Silver, both of London, all of England

[73] Assignee: British Technology Group Ltd., London, England

[21] Appl. No.: 397,321

[22] Filed: Feb. 17, 1995

Related U.S. Patent Documents

Reissue of:

[64] Patent No.: 4,585,780
Issued: Apr. 29, 1986
Appl. No.: 592,271
Filed: Mar. 22, 1984

[30] Foreign Application Priority Data

Mar. 24, 1983 [GB] United Kingdom ..... 8308054

[51] Int. Cl.[6] ..... A61K 31/44; C07D 213/69

[52] U.S. Cl. ..... 514/348; 546/296

[58] Field of Search ..... 546/296; 514/348

[56] References Cited

U.S. PATENT DOCUMENTS

| | | | |
|---|---|---|---|
| Re. 34,313 | 7/1993 | Hider et al. | 514/188 |
| 3,016,372 | 1/1962 | Krimmel | 536/17.4 |
| 3,419,570 | 12/1968 | Brammer et al. | 546/296 |
| 3,847,927 | 11/1974 | Dunbar et al. | 546/296 |
| 3,963,729 | 6/1976 | Gittos et al. | 546/296 |
| 4,131,131 | 12/1978 | Lindenbaum et al. | 137/559 |
| 4,550,101 | 10/1985 | Hider et al. | 514/188 |
| 4,587,240 | 5/1986 | Hider et al. | 514/188 |
| 4,666,927 | 5/1987 | Hider et al. | 514/350 |
| 4,840,958 | 6/1989 | Hider et al. | 514/348 |
| 4,912,118 | 3/1990 | Hider et al. | 514/332 |
| 5,104,865 | 4/1992 | Hider et al. | 514/188 |
| 5,177,068 | 1/1993 | Callingham et al. | 514/184 |

FOREIGN PATENT DOCUMENTS

| | | | |
|---|---|---|---|
| 2808825 | 9/1978 | Germany | 546/296 |
| 3005069 | 8/1981 | Germany | 546/296 |
| 49-87676 | 8/1974 | Japan . | |
| 50-36467 | 4/1975 | Japan . | |
| 59-118792 | 7/1984 | Japan . | |
| 1446409 | 8/1976 | United Kingdom . | |
| 2117766 | 10/1983 | United Kingdom . | |
| 2118176 | 10/1983 | United Kingdom | 546/296 |

OTHER PUBLICATIONS

H. Hashiguchi et al. "Inhibition of two copper–containing enzymes, . . . " Molecular Pharmacology, 13, pp. 362–367.

J. Brammer Petersen, et al. The Chemistry of Endialone, printed in Denmark 1967, pp. 1–23.

C. G. Pitt et al., The Design and Synthesis of Chelating Agents for the Treatment of Iron Overload in Colley's Anemia, Research Triangle Institute, DHEW Publication No. 77–994, 1975.

B. Tamhina et al., Extraction and Spectrophotometric Determination of Iron (III) by 1–Phenyl–2–Methyl–3–Hydroxy–4–Pyridone Croatica Chemica Acta CCACAA 45 (4), 603–610 (1973).

J. A. Berson et al., Spectra as a Guide to Structure in the Hydroxypyrone and Hydroxypyridone Series, Dept. of Chemistry, University of Southern California, 1955.

Jacobs, Screening for Iron Chelating Drugs, Elsevier North Holland, Inc., 1981, pp. 39–46.

Wilson et al., Chelation and Biologic Action, Textbook of Organic Medicinal and Pharmaceutical Chemistry, Third Edition, J. B. Lippincott Company, Philadelphia, Pa., 1956, pp. 25–27.

Chemical Abstracts, vol. 90, #186151m, Jun. 4, 1979.

Chemical Abstracts, vol. 90, #167745s, May 21, 1979.

Chemical Abstracts, vol. 89, #37739m, Jul. 31, 1978.

Chemical Abstracts, vol. 86, #167059p, Jun. 6, 1977.

Chemical Abstracts, vol. 85, #104644j, Oct. 11, 1976.

Chemical Abstracts, vol. 80, #103826e, May 13, 1974.

Chemical Abstracts, vol. 77, #122732a, Nov. 6, 1972.

Journal of Medicinal Chemistry, 17, No. 1, 1974, The American Chemical Society, L. E. Hare et al.: "Aromatic Acid Hydroxylase Inhibitors . . . ".

Chemical Abstracts, vol. 86, #12119e, Jan. 17, 1977.

Bulletin of the Chemical Society of Japan, 52, No. 1, Jan. 1979, K. Imafuku et al.: Substituent Effects on 6–Substituted 3–Hydroxy . . . .

Chemical Abstracts, vol. 85, #143377u, Nov. 8, 1976.

Chemical Abstracts, vol. 76, #71652u, Mar. 27, 1972.

Z. Lebensm. Unters. Forsch., T. Severin et al., 1976, Formation of Pyridone Derivatives from Maltose and Lactose, XII, Investigations on the Maillard . . . .

Bulletin of the Chemical Society of Japan, 52(1), 107–110 (1979) Jan., K. Imafuku et al.: Structure of 5–Hydroxy–2–. . . .

Journal of Medicinal Chemistry, 22, No. 1, Jan. 1979, p. 99, J. G. Atkinson et al., Kojic Amine–a Novel . . .

Chemical Abstracts, vol. 74, #23102b, Feb. 1, 1971.

Chemial Abstracts, vol. 97, #92049a, Sep. 13, 1982.

*Primary Examiner*—Alan L. Rotman
*Attorney, Agent, or Firm*—Nixon & Vanderhye

[57] ABSTRACT

Pharmaceutical compositions containing a 3-hydroxypyrid-2-one or 3-hydroxypyrid one in which the hydrogen atom attached to the nitrogen atom is replaced by an aliphatic acyl group, by an aliphatic hydrocarbon group, or by an aliphatic hydrocarbon group substituted by one or, except in the case of ionizable groups, more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group, or by an aliphatic hydrocarbon group substituted by an alkoxy, aliphatic ester, halogen or hydroxy group, but excluding compounds in which said replacement of hydrogen atoms in the compound is effected only by aliphatic hydrocarbon groups, or a salt thereof containing a physiologically acceptable ion or ions, are of value for removing toxic amounts of metals, particularly iron, from the body.

58 Claims, No Drawings

PHARMACEUTICAL COMPOSITIONS

Matter enclosed in heavy brackets [ ] appears in the original patent but forms no part of this reissue specification; matter printed in italics indicates the additions made by reissue.

This invention relates to compounds for use in pharmaceutical compositions.

Certain pathological conditions such as thalassaemia, sickle cell anaemia idiopathic haemochromatosis and aplastic anaemia are treated by regular blood transfusions. It is commonly found that such transfusions lead to a widespread iron overload, which condition can also arise through increased iron absorption by the body in certain other circumstances. Iron overload is most undesirable since, following saturation of the ferritin and transferrin in the body, deposition of iron can occur and many tissues can be adversely affected, particular toxic effects being degenerative changes in the myocardium, liver and endocrine organs. Such iron overload is most often treated by the use of desferrioxamine. However, this compound is an expensive natural product obtained by the culture of Streptomyces and, as it is susceptible to acid hydrolysis, it cannot be given orally to the patient and has to be given by a parenteral route. Since relatively large amounts of desferrioxamine may be required daily over an extended period, these disadvantages are particularly relevant and an extensive amount of research has been directed towards the development of alternative drugs. However, work has been concentrated on three major classes of iron chelating agents or siderophores, namely hydroxamates, ethylenediamine tetra-acetic acid (EDTA) analogues and catechols. The hydroxamates generally suffer from the same defects as desferrioxamine, being expensive and acid labile, whilst the other two classes are ineffective at removing iron from intracellular sites Moreover, some catechol derivatives are retained by the liver and spleen and EDTA analogues possess a high affinity for calcium and so are also likely to have associated toxicity problems.

We have accordingly studied the iron chelating ability of a wide range of compounds and in UK patent application No. 8308056, published as GB No. 2,118,176A (U.S. application Ser. No. 478,493), we describe a group of compounds which we have identified as being of particular use for the treatment of conditions involving iron overload. These compounds consist of 3-hydroxypyrid-2- and -4-ones in which the nitrogen atom and optionally one or more of the carbon atoms of the ring are substituted by an aliphatic hydrocarbon group, particularly of 1 to 6 carbon atoms. We have now found that 3-hydroxypyrid-2-ones and 3-hydroxypyrid-4-ones containing other ring substituents are also of particular value in the treatment of such conditions.

According to the present invention a pharmaceutical composition comprises a compound being a 3-hydroxypyrid-2-one or 3-hydroxypyrid-4-one in which the hydrogen atom attached to the nitrogen atom is replaced by an aliphatic acyl group, by an aliphatic hydrocarbon group, or by an aliphatic hydrocarbon group substituted by one or, except in the case of ionisable groups, more than one substituent selected from aliphatic acyl, alkoxy, aliphatic amide, aliphatic amine, carboxy, aliphatic ester, halogen, hydroxy and sulpho groups and, optionally, in which one or more of the hydrogen atoms attached to ring carbon atoms are replaced by one of said substituents, by an aliphatic hydrocarbon group, or by an aliphatic hydrocarbon group substituted by an alkoxy, aliphatic ester, halogen or hydroxy group, but excluding compounds in which said replacement of hydrogen atoms in the compound is effected only by aliphatic hydrocarbon groups, or a salt thereof containing a physiologically acceptable ion or ions, together with a physiologically acceptable diluent or carrier.

The ability of both the free compound and its iron complex to permeate membranes is important in the context of the treatment of iron overload, it is also desirable for both to possess some degree of water solubility. A good indication of the physical properties of a compound and its iron complex in this respect is provided by the value of the partition coefficient ($K_{part}$) obtained on partition between n-octanol and tris hydrochloride (20 mM, pH 7.4; tris representing 2-amino-2-hydroxymethylpropane 1,3-diol) at 20° C. and expressed as the ratio (concentration of compound in organic phase)/(concentration of compound in aqueous phase). Preferred compounds show a value of $K_{part}$ for the free compound of above 0.02 or 0.05 but less than 3.0, especially of above 0.2 but less than 1.0, together with a value of $K_{part}$ for the 3:1 hydroxypyridone/iron(III) complex of above 0.02 but less than 6.0, especially of above 0.2 but less than 1.0. The following comments upon preferences among the groups used for replacement of hydrogen atoms attached to nitrogen or carbon atoms of the pyridone ring are directed towards the use of compounds having partition coefficients in the free and complexed state which lie in these preferred ranges. For examples of measured partition coefficients of specific compounds reference should be made to Table 1 of Example 25.

Compositions of particular interest are those containing a compound in which the hydrogen atom attached to the nitrogen atom of the pyridone ring is replaced by a group other than an aliphatic hydrocarbon group, although the invention does of course extend to compositions containing a compound in which this hydrogen atom is replaced by an aliphatic hydrocarbon group and a hydrogen atom attached to a carbon atom of the ring is replaced by another type of group. Furthermore, although compounds having a group other than an aliphatic hydrocarbon group attached to the ring nitrogen atom may also have the hydrogen atom of one or more ring carbon atoms replaced by the same or a different group which is also other than an aliphatic hydrocarbon group, it is preferred either that the ring carbon atoms in such compounds are unsubstituted or that substitution is limited to aliphatic hydrocarbon groups.

More than one of the ring carbon atoms of the 3-hydroxypyrid-2- or -4-one may be substituted, for example two of such atoms, either by the same substituent group or by different substituent groups, for example by an aliphatic hydrocarbon group and by another type of substituent, although compounds in which none or only one of the ring carbon atoms are substituted, for example by an aliphatic hydrocarbon group, are preferred. Substitution of these atoms is of more interest with the 3-hydroxypyrid-4-ones, for example at the 6- or particularly the 2-position, than with the 3-hydroxypyrid-2-ones. Particularly when the ring carbon atoms are substituted by the larger groups, however, there may be an advantage in avoiding substitution on a carbon alpha to the

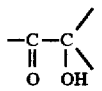

system. This system is involved in the complexing with iron and the close proximity of one of the larger aliphatic hydrocarbon groups may lead to steric effects which inhibit complex formation.

Where a ring nitrogen or carbon atom is substituted by an aliphatic hydrocarbon group, this group may be cyclic or acyclic, having a branched chain or especially a straight chain in the latter case, and may be unsaturated or especially saturated. Groups of from 1 to 6 carbon atoms, particularly of 1 to 4 and especially of 1 to 3 carbon atoms, are of most interest. Alkyl groups are preferred, for example cyclic groups such as cyclopropyl and especially cyclohexyl but, more particularly preferred are acyclic groups such as methyl, ethyl, n-propyl and isopropyl. Where the ring carbon atoms are substituted by an aliphatic hydrocarbon group or groups these are preferably methyl but in the case of a group substituting the nitrogen atom larger groups may more often be utilised with particular advantage.

In the case of substituted aliphatic hydrocarbon groups, the preferences as to the nature of the aliphatic hydrocarbon group are broadly as expressed above but the preferences as to size are somewhat different. Firstly, in the case of such groups attached to nitrogen, groups containing only 1 carbon atom are of less interest, particularly with certain substituent groups such as hydroxy and amine groups, since compounds containing such substituted groups may be difficult to prepare because of a relative lack of stability of the systems

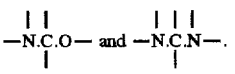

Furthermore, in the case of substituted aliphatic hydrocarbon groups attached both to nitrogen and to carbon atoms, a substituted methyl group containing a hydrophilic substituent may cause the compound to be of too hydrophilic a character unless the effect of this group is balanced by that of another, more hydrophobic, group. For this reason aliphatic hydrocarbon groups of 2 or especially 3 or more carbon atoms are often preferred in this context, particularly where the substituent is an amine, carboxy, hydroxy or sulpho group, although groups of 1 or 2 carbon atoms may be very suitable in certain cases, for example where the substituent is an amide group, particularly an N-substituted one. It will be appreciated therefore, that the range of size of aliphatic hydrocarbon groups which are substituted may conveniently be greater than that indicated above as being preferred for unsubstituted groups, for example 1 to 8 carbon atoms, particularly 1 to 6 carbon atoms, and especially 3, 4 or 5 carbon atoms when the substituted group contains no additional hydrophobic group.

In general, the circumstances in which the smaller substituted aliphatic hydrocarbon groups are of interest occur either when the substituent group involved is not of a particularly hydrophilic character or when it is of such a character but an additional group, such as a larger aliphatic hydrocarbon group of, for example, 3 or more carbon atoms is present to provide a balance to the hydrophilic character. Such a larger group may be present in the same substituted aliphatic hydrocarbon group, as is the case with the amide containing groups referred to above, or separately. In particular, when both the ring nitrogen atom and one or more of the ring carbon atoms carry a substituted aliphatic hydrocarbon group, it may be suitable for one of the substituted aliphatic hydrocarbon groups, for example that carried by the nitrogen atom, to be of a size as discussed above, for example of 3 or 4 to 5 or 6 carbon atoms, and for the other or others to be smaller, for example of 2 or particularly 1 carbon atom. Thus, when the nitrogen atom carries either a substituted aliphatic hydrocarbon group or an acyl group, and also a hydrogen atom or atoms attached to carbon are replaced, then such replacement, for example at the 6-position, as an alternative or in addition to being effected by an aliphatic hydrocarbon group, may conveniently be effected by a substituted methyl group. It will be appreciated that substitution at the nitrogen atom of the compounds is of particular interest in the present invention and that it is preferred to dictate the hydrophilic/hydrophobic balance in the molecule primarily through such N-substitution. It is more usually the case therefore that, when the compounds are C-substituted but the preferred form of C-substitution involving aliphatic hydrocarbon groups is not present, the C-substituent or substituents incorporate substituted aliphatic hydrocarbon groups which are such that preferences as to the size and nature of these groups are broadly as expressed for the unsubstituted groups, for example being substituted alkyl groups of 1 to 3 carbon atoms and particularly substituted methyl groups such as chloromethyl, ethoxymethyl, and especially hydroxymethyl.

Substituted aliphatic hydrocarbon groups attached to the nitrogen atom of compounds of use in the present invention may contain more than one substituent, for example two substituents of a different type. One example of such a multiply substituted aliphatic hydrocarbon group occurs where the group is substituted both by a sulphonic or particularly a carboxylic acid ester group and by a sulphonic or particularly a carboxylic acid amide group. One potential drawback with such multiply substituted groups, however, is their increased size and it is the case, therefore, that groups containing one substituent, often terminally substituted on the aliphatic hydrocarbon group, are more commonly employed and, as indicated hereinbefore, substitution by more than one ionisable group (amine, carboxy or sulpho) is specifically excluded (substitution by more than one group, only one of which is ionisable, is not excluded although not of great interest).

As regards the substituent groups present in the compounds of use in the present invention, an aliphatic acyl group may contain a sulphonyl or carbonyl group. The latter type are however preferred and although the acyl group may be a formyl group, alkylcarbonyl groups are of most interest. Such acyl groups may, for example, be of 2 to 4 or 5 carbon atoms, and particularly may contain alkyl groups of the type described above as being preferred as an aliphatic hydrocarbon group substituent at a ring nitrogen or carbon atom being, for example, $—COCH_2CH_3$ or especially $—COCH_3$. Alkoxy groups may conveniently be of 1 to 4 carbon atoms and contain similar alkyl groups to those which are preferred in the alkylcarbonyl groups, examples of such substituents being ethoxy and particularly methoxy.

Amine substituents may consist of a group $—NH_2$ or its charged equivalent, a group $—N^+H_3$ which will be associated with a physiologically acceptable anion, for example a chloride or other halide ion, a solubilising ion such as that from methane sulphonic or isethionic acid, or an anion derived from the hydroxy group of the ring ($OH \rightarrow O^-$), or such a $—NH_2$or $—N^+H_3$ group in which one or more of the atoms is replaced by an aliphatic hydrocarbon group, for example an alkyl group such as is described above as a substitutent at a ring nitrogen or carbon atom. Amide substituents may contain a sulphonyl or a carbonyl group. The latter type are, however, of most interest and the further discussion will therefore refer to them although it applies equally to the sulphonyl type. The amide substituent may be of the unsubstituted form $—ONH_2$ or may contain a nitrogen atom which is mono- or di-substituted as just described for the amine substituents, for example being a group $—CONHCH_3$, etc. Alternatively, the $$-\overset{|}{CO.N}-$$

grouping of the amide substituent may be arranged in the opposite sense so that in an N-substituent, for example, the nitrogen atom of the amide grouping is linked to the aliphatic hydrocarbon group which is attached to the nitrogen atom of the ring, the carbonyl group being attached to an aliphatic hydrocarbon group, for example an alkyl group such as is described above is a substituent at a ring nitrogen or carbon atom, or in the case of a carboxylic acid amide but not in that of a sulphonic acid amide, to hydrogen. In the case of an amide group arranged in this opposite sense, the nitrogen atom may carry a hydrogen atom or be monosubstituted as discussed for amide substituents of the first mentioned form, that form of amide substituent being the one of particular interest.

Carboxy and sulpho substituents may be present as the group $—O_2H$ or $—S_3H$, or as the anion derived therefrom in combination with a physiologically acceptable cation, for example the cation of an alkali metal such as sodium, quaternary ammonium ions or protonated amines such as the cation derived from tris (tris represents 2-amino-2-hydroxymethyl propane 1,3-diol). Ester substituents may contain a sulphonyloxy or preferably a carbonyloxy group and may be arranged in either sense, i.e. with a carboxylic acid ester the group —CO.O— may have either the carbonyl group or the oxy group linked to the carbon atom of the ring or the nitrogen atom of the ring (through an aliphatic hydrocarbon group on which the ester group is substituted, where appropriate). The other group of oxy and carbonyl will be linked to an aliphatic hydrocarbon group forming part of the ester group or, in the case where this is a carbonyl group may alternatively be linked to hydrogen (this possibility does not apply in the case of sulphonic acid esters). Once again, preferred aliphatic hydrocarbon groups contained by the ester group are those described above as substituents in relation to substitution on a ring nitrogen or carbon atom. In the case of N-substituents, where the ester group is attached to an aliphatic hydrocarbon group which is in turn attached to the ring, ester groups in which the carbonyl or sulphonyl group is linked to this aliphatic hydrocarbon group are preferred, for example the groups $—CH_2CO_2CH_3$ and $—CH_2CO_2C_2H_5$. In the case of C-substituents the reverse is true and with any C-substituent consisting of an aliphatic hydrocarbon group substituted by an ester group there is a strong preference for the oxy group to be attached to the aliphatic hydrocarbon group which is in turn attached to the ring, for example as in the groups $—H_2O.COCH_3$ and $—CH_2O.COC_2H_5$. Halogen substituents may conveniently be iodo, fluoro, bromo or especially chloro.

It should be noted that sulphonic acid groups and the corresponding ester and amide groups are of less interest as N-substituents in the case of the pyrid-2-ones than in that of the pyrid-4-ones but that N-substituents consisting of an aliphatic hydrocarbon group substituent by an acyl group are of most interest in the case of the pyrid-2-ones.

Among the substitutents on the ring nitrogen atom of some particular interest are aliphatic acyl groups and aliphatic hydrocarbon groups substituted by amine, amide, carboxy, aliphatic ester and hydroxy groups, for example the groups $—COR_1$, $—(CH_2)_n—COXR_2$ and $—(CH_2)_m—XH$, and to a lesser extent the more complex type of group $—(CH_2)_nCH(COY)NHCOR_2$, in which $R_1$ is an alkyl group, for example methyl, ethyl or n-propyl, $R_2$ is hydrogen or an alkyl group, for example methyl, ethyl, n-propyl, isopropyl or butyl, or X is an oxy or imino group, Y is $OR_1$ or $NR_2$, n is an integer from 1 to 4 or 6, particularly 2, 3 or 4 and m is an integer from 2 to 4 or 6 particularly 3, 4 or 5. It will be appreciated that there is an inter-relation between the preferred values of n and $R_2$ so that the groups having the higher values of n tend to have the lower values of $R_2$, and vice versa, so that in groups $—(CH_2)_n—COXR_2$, for example, $—(CH_2)_n—$and $R_2$ may conveniently together contain 3 to 7 carbon atoms, especially 4 to 6 carbon atoms. Also of interest as N-substitutents in the case where a ring carbon atom is substituted by other than an aliphatic hydrocarbon group are aliphatic hydrocarbon groups, for example groups $R_1$, $R_1$ being as described above.

Among substituents on the ring carbon atoms which are of some particular interest are aliphatic hydrocarbon groups and such groups substituted by a halogen, alkoxy or especially a hydroxy group, for example the groups $R_1$, $—CH_2Cl$, $—CH_2OC_2H_5$ and $—CH_2OH$ in which $R_1$ is as described above.

The N-substituents described above may be present on the nitrogen atoms of various 3-hydroxypyrid-2-ones and 3-hydroxypyrid-4-ones, in particularly 3-hydroxypyrid-2-one, 3-hydroxypyrid-4-one, 2-alkyl (e.g. methyl and ethyl)-3-hydroxypyrid-4-ones, 6-alkyl-(e.g. methyl)-3-hydroxypyrid-4-ones, 2,6-dialkyl(e.g. dimethyl)-3-hydroxypyrid-4-ones and 3-hydroxy-6-hydroxymethyl-pyrid-4-one. In the case of the 3-hydroxypyrid-2-ones, N-substituent groups of the aliphatic acyl, and amide- and ester-substituted aliphatic hydrocarbon group type are of especial interest, whilst in the case of the 3-hydroxypyrid-4-ones, N-substituent groups of the aliphatic acyl and amide-, ester- and hydroxy-substituted aliphatic hydrocarbon group type are of especial interest.

As indicated above, the compounds may contain substituent groups, particularly an aliphatic amine, carboxy or sulpho group, in the salt form. Additionally, the compounds may, if desired, be used in the form of salts formed at the hydroxy group thereof through its conversion to the anion ($OH \rightarrow O^-$) and containing a physiologically acceptable cation, for example the cation of an alkali metal such as sodium, quaternary ammonium ions or protonated amines such as the cation derived from tris (tris represents 2-amino-2-hydroxymethyl propane 1,3-diol). Salt formation may be advantageous in increasing the water solubility of a compound but, in general, the use of the compounds themselves rather than their salts, is preferred.

Specific examples of N-substituted 3-hydroxypyrid-2-and -4-ones lacking C-substitution other than by an aliphatic hydrocarbon group are the following compounds, with the various symbols being as defined above and R being hydrogen, ethyl or especially methyl, whilst p represents 0,1,2,3 or 4 (the case of $R_2$=H being of less interest when p=0). Compounds (IV) in which X is an oxy group and compounds (II), and also (V), in which it is an imino group may be mentioned particularly.

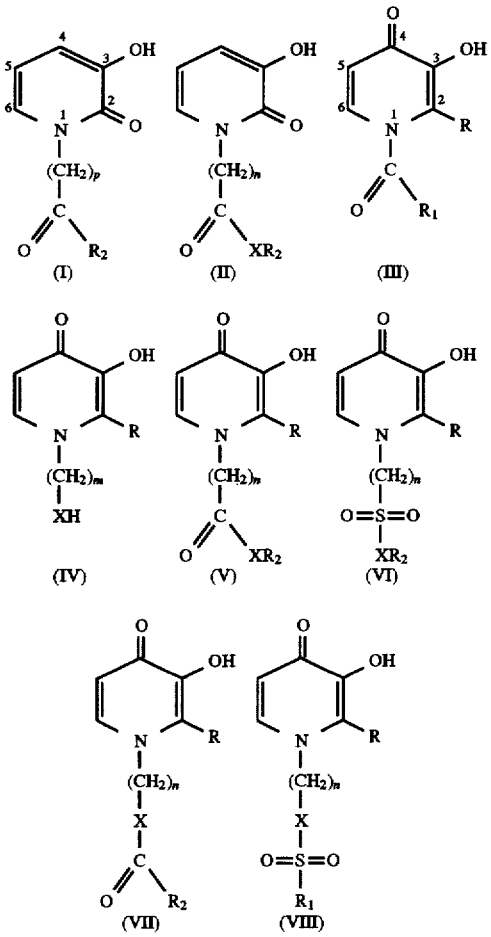

Examples of pyridones containing C-substituents other than aliphatic hydrocarbon groups and N-substituents which are aliphatic hydrocarbon groups are the 1-alkyl-6-halomethyl-3-hydroxypyrid-4-ones and the 1-alkyl-3-hydroxy-6-hydroxymethylpyrid-4-ones and their 6-alkoxymethyl analogues, specific examples of which are the following compounds in which the various symbols are as defined above, the two symbols $R_1$ representing the same or a different alkyl group in (XI), and Hal represents a halogen group.

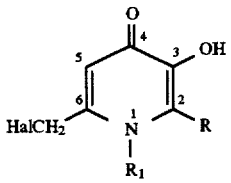

(IX)

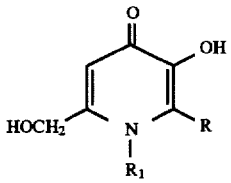

(X)

-continued

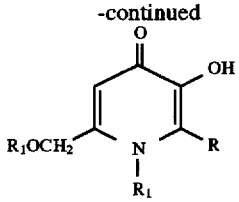

(XI)

Although both types of compound are of interest in the context of the present invention, the 3-hydroxypyrid-4-ones are of particular interest, whilst the 3-hydroxypyrid-2-ones are the compounds of particular interest when the compounds described herein are used in the form of their iron complexes for the treatment of iron deficiency anaemia as described in another UK patent application of even date herewith.

3-Hydroxy-6-hydroxymethyl-1-methylpyrid-4-one, 1-(2'-aminoethyl)-3-hydroxypyrid-4-one, 3-hydroxy-1-(2'-hydroxyethyl)-2-methylpyrid-4-one, 1-carboxymethyl-3-hydroxy-2-methylpyrid-4-one and 1-methoxycarbonylmethyl-3-hydroxy-2-methyl-pyrid-4-one are known compounds but all of the other compounds described above are believed to be novel. The present invention thus also includes as compounds, per se, a 3-hydroxypyrid-2-one or 3-hydroxypyrid-4-one in which the hydrogen atom attached to the nitrogen atom is replaced by an aliphaitc acyl group, by an aliphatic hydrocarbon group, or by an aliphatic hydrocarbon group substituted by one or, except in the case of ionisable groups, more than one substituent selected from aliphatic acyl, alkoxy, aliphatic mine, aliphatic amide, carboxy, aliphatic ester, halogen, hydroxy and sulpho groups and, optionally in which one or more of the hydrogen atoms attached to ring carbon atoms are replaced by one of said substituents, by an aliphatic hydrocarbon group, or by an aliphatic hydrocarbon group substituted by an alkoxy, aliphatic ester, halogen or hydroxy group, but excluding compounds in which said replacement of hydrogen atoms in the compound is effected only by aliphatic hydrocarbon groups, or a salt thereof with a physiologically acceptable ion or ions, excluding the specific compounds 3-hydroxy-6-hydroxymethyl-1-methylpyrid-4-one, 1-(2'-aminoethyl)-3-hydroxypyrid-4-one, 3-hydroxy-1-(2'-hydroxyethyl)-2-methylpyrid-4-one, 1 carboxymethyl-3-hydroxy-2-methylpyrid-4-one and 1-methoxycarbonylmethyl-3-hydroxy-2-methylpyrid-4-one The 3-hydroxy-pyrid-2-one compounds may conveniently be prepared by nucleophilic substitution at the nitrogen atom of the corresponding 2,3-dihydroxypyridine or one containing groups convertible to C-substitutents present in the desired pyridone, for example using an organic halide R'X in which R' represents the group present on the nitrogen atom of the desired 3-hydroxypyrid-2-one or a group convertible thereto and X represents a halogen group. In particular, X may for example represent an iodo group when R' represents an aliphatic hydrocarbon group or such a group of 2 or more carbon atoms substituted by an aliphatic acyl group such as $CH_3CO(CH_2)_2$—, or a bromo group when R' represents an aliphatic acyl group, such as $CH_3CO$— or $CH_3CH_2CO$—, an aliphatic hydrocarbon group substituted by an aliphatic acyl group, such as $CH_3COCH_2$—, or an aliphatic ester group, such as $C_2H_5OCOCH_2$—. A group of the last mentioned type, once introduced into the nitrogen atom, may be hydrolysed to yield an aliphatic hydrocarbon group substituted by a carboxy (or sulpho) group, which carboxy (or sulpho) group may in turn be converted to an amide group or even another ester group.

The 3-hydroxypyrid-4-one compounds may conveniently be prepared similarly or preferably from the more readily accessible corresponding 3-hydroxy-4-pyrone or a 3-hydroxy-4-pyrone containing groups convertible to the C-substituent present in the desired pyridone, for example by the reaction $—CH_2OH \rightarrow —CH_2Hal$. Thus, the 3-hydroxy-4-pyrone may conveniently be converted to the 3-hydroxypyrid-4-one through protection of the hydroxy groups, for example as an ether group such as a benzyloxy group, reaction of the protected compound with a compound $R'NH_2$, in which R' the group present on the nitrogen atom of the desired 3-hydroxypyrid-4-one or a group convertible thereto, in the presence of a base, for example an alkali metal hydroxide such as sodium hydroxide. The hydroxy protecting group may then be removed and any other modifications of the C-substituents effected. In particular R' may for example represent an aliphatic hydrocarbon group, a hydroxyamine, such as 2-hydroxyethylamine, or 3-hydroxypropylamine, a diamine, such as ethylenediamine, or an amino acid, such as glycine, α- or β-alanine, γ-aminobutyric acid or taurine. Hydroxy, amine and carboxy (or sulpho) groups in N-substituents may of course be converted to ester, amide and ester groups, respectively.

An alternative procedure involves the use of a 2-aliphatic acyl 3-hydroxyfuran which may be reacted with a compound $R'NH_2$, the reaction, for example, of 2-acetyl-3-hydroxyfuran with the sodium salt of glycine to form 1-carboxymethyl-3-hydroxy-2-methylpyrid-4-one being described by Severin and Loidl in Z. Lebensm. Unters.-Forsch. 1976, 161, 119.

An example of the modification of C-substituents after formation of the pyridone ring arises in the case where it is appropriate for substituents on carbon atoms of the ring to be protected whilst substitution is effected at the nitrogen atom of the ring. Thus, for example, where a hydroxymethyl group is present on the ring as well as the 3-hydroxy group, both hydroxy groups in a 3-hydroxy-4-pyrone may be protected as described above. Moreover, N-acylated pyrid-4-ones may be prepared by direct acylation but it is preferred to protect the 3-hydroxy group, for example as an ether group such as in benzyloxy group, and to remove this protecting group after the N-acylation has been effected. A similar form of protection of the 3-hydroxy group is suitable where a 6-hydroxyalkyl group is present which is being modified, for example to give a 6-alkoxyalkyl or 6-haloalkyl group.

It will be appreciated from the foregoing that in many cases the final stage in the preparation of the compound comprises deprotecting the hydroxy group of a pyridone having similar ring carbon atom substituents but with the 3-hydroxy group in protected form and either the same ring nitrogen atom substituent or one convertible thereto and, where applicable, converting the N-substituent to that present in said compound and/or, optionally, converted the compound to a salt thereof containing a physiologically acceptable ion or ions.

The compounds may be converted to salts formed between a physiologically acceptable ion or ions and one or both of (a) the anion produced by the loss of the hydroxy group proton and (b) an anionic or cationic group derived from an appropriate substituent, such as one which is or which contains a carboxy, sulpho or amino group, by reaction of the compound with the appropriate base or acid according to standard procedures (amino substituted compounds of a zwitterion type containing a cation from the amino group and an anion from the 3-hydroxy group may be prepared by crystallisation from aqueous media at a pH of about 9).

In general, it is preferred that the compounds are isolated in substantially pure form, i.e. substantially free from by-products of manufacture.

It will be appreciated that these are not the only routes available to these compounds and that various alternatives may be used as will be apparent to those skilled in the art, as will be the routes to the various intermediates required such as C-substituted 2,3- and 3,4-dihydroxypyridines and 3-hydroxy-4-pyrones.

Moreover, it will be appreciated that certain of the compounds may be converted in vivo to other compounds which will be involved for the metal binding activity observed in vivo. This will be true, for example, of compounds containing ester groups which are likely to be converted to carboxy groups when the compounds are administered orally.

The compounds may be formulated for use as pharmaceuticals for veterinary, for example in an avian or especially a mammalian context, or particularly human use by a variety of methods. For instance, they may be applied as an aqueous, oily or emulsified composition incorporating a liquid diluent which most usually will be employed for parenteral administration and therefore will be sterile and pyrogen free. However, it will be appreciated from the foregoing discussion in relation to desferrioxamine that oral administration is to be preferred and the compounds of the present invention may be given by such a route. Although compositions incorporating a liquid diluent may be used for oral administration, it is preferred, particularly in humans, to use compositions incorporating a solid carrier, for example a conventional solid carrier material such as starch, lactose, dextrin or magnesium stearate. Compositions comprising a diluent of water and/or an organic solvent which are non-sterile are therefore of less interest. Such solid compositions may conveniently be of a formed type, for example as tablets, capsules (including spansules), etc.

Other forms of administration than by injection or through the oral route may also be considered in both human and veterinary contexts, for example the use of suppositories for human administration.

Compositions may be formulated in unit dosage form, i.e. in the form of discrete portions each comprising a unit dose, or a multiple or sub-multiple of a unit dose. Whilst the dosage of active compound given will depend on various factors, including the particular compound which is employed in the composition, it may be stated by way of guidance that satisfactory control of the amount of iron present in the human body will often be achieved using a daily dosage of about 0.1 g to 5 g, particularly of about 0.5 g to 2 g, veterinary doses being on a similar g/Kg body weight ratio. However, it will be appreciated that it may be appropriate under certain circumstances to give daily dosages either below or above these levels. Where desired, more than one compound according to the present invention may be administered in the pharmaceutical composition or, indeed, other active compounds may be included in the composition.

It has never before been appreciated that compounds such as those described herein might be used in a pharmaceutical context, and with real advantage. We have found that the 3-hydroxypyrid-2-and -4-ones described above are particularly suited to the removal of iron from patients having an iron overload. The compounds form neutral 3:1 iron complexes at most physiological pH values, and have the advantage that they do not co-ordinate calcium or magnesium. Both the compounds and their complexes will partition into n-octanol indicating that they will permeate biological membranes, this property being confirmed in practice by tests of the ability of the $^{59}Fe$ labelled iron complexes to permeate erythrocytes.

Both the 3-hydroxypyrid-2-ones and the 3-hydroxypyrid-4-ones possess a high affinity for iron (III), as evidenced by log $K_{sol}$ values {log $K_{sol}$ is defined as being equal to log $\beta_{Fe(L)n}$+21-[$pK_{sp}$+n log $a_{L(H+)}$+m log $a_L$(Ca+ +)] where log $\beta_{Fe(L)n}$ is the cumulative affinity constant of the ligand in question for iron (III), $pK_{sp}$ is the negative logarithm of the solubility product for $Fe(OH)_3$ and has a value of 39, n and m are the number of hydrogen and calcium ions, respectively, which are bound to the ligand, and $a_{L(H+)}$ and $a_L$(Ca+ +) are the affinities of the ligand for hydrogen ions and calcium ions, respectively}. In order to solubilise iron (III) hydroxide, log $K_{sol}$ must be greater than 0 and in order to remove iron from transferrin, log $K_{sol}$ should be in excess of 6.0. The log $K_{sol}$ values for 3-hydroxy-1-methylpyrid-2-one and 1,2-dimethyl-3-hydroxypyrid-4-one, by way of example, are 10.0 and 9.5, respectively, thus comparing favourably with those of the bidentate hydroxamates at about 4.0, of catechols at about 8.0, of desferrioxamine at 6.0, and of diethylenetriamine pentaacetic acid (DTPA) at 2.0. Moreover, the ability of the compounds to remove iron efficiently has been confirmed both by in vitro tests and also by in vivo tests in mice. It is particularly significant that these latter tests are successful whether the compound is given intraperitoneally or orally by stomach tube, the compounds generally either being stable under acidic conditions or being converted thereby to acid stable active compounds. Oral activity is not generally present among the other types of compound previously suggested for use as iron coordinating drugs and although certain EDTA analogues do show such activity, they possess drawbacks for pharmaceutical use.

In addition to the use described hereinbefore for the treatment of general iron overload, the 3-hydroxypyridones described herein are also of interest for use in certain pathological conditions where there may be an excess of iron deposited at certain sites even though the patient does not exhibit a general iron overload, this being the case, for example, in certain arthritic and cancerous conditions. Indeed in some patients having such conditions, the patient may exhibit an overall anaemia and in a further UK patent application in our name of even date herewith the use is described of the metal-free compounds of the present invention in conjunction with an iron complex for the treatment of such patients. Thus, a mixture of an iron complex of a 3-hydroxypyridone as described herein together with one of the 3-hydroxypyridones in metal-free form will have the effects of remedying the overall anaemia through the action of the iron complex whilst the metal-free compound will act to remove iron from pathological to physiological sites.

Although the major use of the compounds is in the removal of iron, they are also of potential interest for the removal of some other metals present in the body in deleterious amounts for example copper, and especially aluminum. The present invention thus includes the use of a 3-hydroxypyrid-2- or -4-one or salt thereof as described hereinbefore for use in medicine, for example for the removal from the body of toxic amounts of metals, particularly iron. Moreover, the invention also includes a method for the treatment of a patient having toxic amounts of a metal, particularly iron, in the body which comprises administering to said patient an amount of a 3-hydroxypyrid-2-or 4-one or salt thereof as described hereinbefore to effect a reduction of the levels of this metal in the patient's body.

Uses of the compounds of the present invention for combination with metals other than iron may extend to the treatment of body fluids outside the body or even to quite other contexts than the treatment of patients. One particular area of some interest involves the treatment of patients on haemodialysis who may show a dangerous build up of aluminum in the body. For the treatment of such patients the compounds of the present invention may be attached to a support material and then contacted with the patient's blood to remove aluminum therefrom. The support material may conveniently be one of various types of polymer described in the art for use in similar contexts, for example a carbohydrate material which may be an agarose, dextran or other type, or a polystyrene or other material such as is used in ion-exchange resins.

Various approaches known in the art may be used for effecting attachment of the compounds to such support materials but one convenient approach is to use an acidic or basic group on the support material to provide an amide type linkage through reaction with the hydroxypyridone. Hydroxypyridones of particular interest in this context are those containing acidic or basic substituents on a ring carbon or particularly on the ring nitrogen atom. Of particular interest are hydroxypyridones which contain an N-substituent which is an aliphatic hydrocarbon group substituted by an aliphatic amine or a sulpho or especially a carboxy group. The present invention thus further comprises a 3-hydroxy hydroxypyrid-2- or -4-one as defined hereinbefore linked to a support material through one of said substituents.

This invention is illustrated by the following Examples.

EXAMPLES

EXAMPLE 1

The preparation of 1-acetyl-3-hydroxypyrid-2-one 2,3-Dihydroxypyridine (5.55 g) is refluxed with acetylbromide (10 ml) overnight. The reaction mixture is allowed to cool and water (10 ml) is added. The resulting suspension is extracted with methylene chloride and the methylene chloride solution is dried over $Na_2SO_4$ and evaporated. The resultant residue is recrystallised from petroleum ether (80°–100° C.) to give 1-acetyl-3-hydroxypyrid-2-one as white crystals (2.8 g), m.p. 140°–141° C.; $\nu_{max}$ (nujol) 1680, 3120 $cm^{-1}$; $\delta(d_6DMSO)$, 2.2 (s, 3H), 6.1 (t, 1H), 6.65 (m, 1H), 7.2 (d, 1H)

EXAMPLE 2

The preparation of 1-ethoxycarbonlmethyl-3-hydroxypyrid-2-one 2,3-Dihydroxypyridine (5 g) is suspended in ethylbromoacetate (20 ml) and the mixture heated in a sealed tube for 24 hours at 140° C. The tube is then cooled in solid $CO_2$ and opened. The contents are subjected to rotary evaporation at 50° C. to yield a yellow solid. Recrystallisation of this solid from water yields 1-ethoxycarbonylmethyl-3-hydroxypyrid-2-one as white crystals (5.4 g), m.p. 141°–151° C.; $\nu_{max}$ (nujol) 1645, 1720 $cm^{-1}$; $\delta(d_6DMSO)$, 1.0 (t, 3H), 4.0 (q, 2H), 4.55 (s, 2H), 5.95 (t, 1H), 6.6(d, 1H), 7.05 (d, 1H).

EXAMPLE 3

The preparation of 1-carboxymethyl-3-hydroxypyrid-2-one

1-Ethoxycarbonylmethyl-3-hydroxypyrid-2-one (2 g) is dissolved in 15 ml of 1:2 v/v ethanol/water containing sufficient ammonium hydroxide to create a pH of 12.0. The solution is heated at 60° C. for 30 minutes, cooled, and acidified to pH 3.0 by the addition of formic acid. The solution is rotary evaporated to remove most of the ethanol and then freeze dried for 20 hours to remove the water, formic acid and ammonium formate. The resulting solid is recrystallised from water to yield white crystals (1.4 g), m.p. 203°–205° C.; $\nu_{max}$ (nujol) 1540, 1590, 1640, 1695, 3240 $cm^{-1}$; δ($d_6$DMSO) 4.5 (s, 2H), 5.95 (t, 1H), 6.6 (d, 1H), 7.0 (d, 1H).

EXAMPLE 4

The preparation of 3-hydroxy-1-methoxycarbonylmethylpyrid-2-one

1-Carboxymethyl-3-hydroxypyrid-2-one (1 g), prepared as described under Example 3, is refluxed in methanolic hydrochloric acid for 2 hours. The solvent is removed by rotary evaporation and the residue recrystallised from water to give 3-hydroxy-1-methoxycarbonylmethylpyrid-2-one in 60% yield, m.p. 141°–142° C.; $\nu_{max}$ (nujol) 1560, 1595, 1645, 1730, 3220 $cm^{-1}$; δ($d^6$DMSO) 3.55 (s, 3H), 4.65 (s, 2H), 6.05 (t, 1H), 6.7 (d, 1H), 7.1 (d, 1H) 9.2 (s, 1H).

EXAMPLE 5

The preparation of 1-(N-ethylcarbamoylmethyl)-3-hydroxypyrid-2-one

3-Benzyloxy-1-carboxymethylpyrid-2-one

1-Ethoxycarbonylmethyl-3-hydroxypyrid-2-one (10 g), prepared as described under Example 2, is dissolved in methanol/water (9:1 v/v) (400 ml). To this solution is added benzyl chloride (3 molar excess) and NaOH until the pH is above 12. The mixture is then refluxed for six hours to give a clear orange solution. The methanol is removed by rotary evaporation and the aqueous solution is extracted with dichloromethane to remove excess benzyl chloride. The aqueous phase is diluted slightly by adding extra water and then acidified to pH 2 using concentrated hydrochloric acid which results in the precipitation of a beige solid. The mixture is cooled and the precipitate filtered off and washed with diethyl ether. The crude product is recrystallised from ethanol to give 3-benzyloxy-1-carboxymethylpyrid-2-one (5.4 g 41%), m.p. 176°–177° C.

3-Benzyloxy-1-(succinimido-oxycarbonylmethyl)-pyrid-2-one

3-Benzyloxy-1-carboxymethylpyrid-2-one (2 g) is dissolved in dimethylformamide (DMF) (25 ml) and to this solution is added N-hydroxysuccinimide (1 g). The resultant solution is cooled and to it is added dicyclohexylcarbodiimide (DCCI) (11.8 8) in DMF (5 ml). The mixture is allowed to stand overnight to give a brown supernatant and a white precipitate. The precipitate is filtered off, washed with a little DMF and then evaporated to dryness under high vacuum. The crude product is dissolved in a minimum volume of dichloromethane and diethyl ether is added to this solution until it becomes cloudy. The solution is then cooled and the resultant precipitate is filtered off and washed with a little diethyl ether to give 3-benzyloxy-1-succinimidooxycarbonylmethyl)-pyrid-2-one (2.26 g, 82%), m.p. 187°–188° C.

3-Benzyloxy-1-(N-ethylcarbamoylmethyl)-pyrid-2-one

3-Benzyloxy1-(succinimido-oxycarbonylmethyl)-pyrid-2-one (1 g) is dissolved in dichloromethane (100 ml) and to this solution is added ethylamine in a 2 molar excess. The mixture is allowed to stand for five minutes and then the N-hydroxysuccinimide liberated by the reaction is extracted with 1M sodium bicarbonate (2×25 ml). The organic layer is dried over anhydrous sodium sulphate, filtered, and evaporated to give 3-benxyloxy-1-(N-ethylcarbamoylmethyl)-pyrid-2-one as a grey solid in 50% yield, m.p. 171°–172° C.

1-(N-ethylcarbamoylmethyl)-3-hydroxypyrid-2-one

3-Benzyloxyl-(N-ethylcarbamoylmethyl)-pyrid-2-one (1 g) is dissolved in 50:50 v/v aqueous ethanol. Platinum/carbon catalyst (100 mg) is added and the solution is hydrogenated at 20° C. and atmospheric pressure for eight hours. The mixture is filtered, the filtrate subjected to rotary evaporation and the resulting residue recrystallised from ethanol to give 1-(N-ethylcarbamoylmethyl)-3-hydroxypyrid-2-one in 70% yield, m.p. 214°–215 C., $\nu_{max}$ (nujol) 1555, 1580, 1645, 1675, 3260, 3400 $cm^{-1}$, δ($d_6$DMSO) 1.0 (t, 3H, 3.05 (m, 2H), 4.5 (s,2H), 6.05 (t, 1H), 6.7 (d, 1H), 7.05 (d, 1H), 8.2(s, 1H).

EXAMPLE 6

The preparation of 3-hydroxy-1-(N-methylcarbamoylmethyl)-pyrid-2-one

3-Benzyloxy-1-(succinimido-oxycarbonylmethyl)-pyrid-2-one (1 g), prepared as described under Example 5, is reacted with methylamine under substantially similar conditions to those described under (E) for the reaction of this compound with ethylamine to give 3-benzyloxy-1-(N-methylcarbamoylmethyl)-pyrid-2-one as a white solid in 84% yield, m.p.=182°–183° C.

This compound is hydrogenated as described under (E) for the corresponding ethyl analogue to give 3-hydroxy-(N-methylcarbamoylmethyl)-pyrid-2-one in 60% yield, m.p.= 204°–205° C.; $\nu_{max}$ (nujol) 1560, 1585, 1645, 1685, 2950, 3275 $cm^{-1}$. δ($d_6$DMSO) 2.40, 2.46 (2×s, 3H), 4.35 (s, 2H), 6.55 (d, 1H), 6.95 (d, 1H), 7.95 (s, 1H).

EXAMPLE 7

The preparation of 3-hydroxy-1-(N-propylcarbamoylmethyl)-pyrid-2-one

3-Benzyloxy-1-(succinimido-oxycarbonylmethyl)-pyrid-2-one (1 g), prepared as described under Example 5, is reacted with n-propylamine under substantially similar conditions to those described under Example 5 for the reaction of this compound with ethylamine to give 3-benzyloxy-1-(N-propylcarbamoylmethyl)-pyrid-2-one as a beige solid in 60% yield, m.p. 156°–57° C. This compound is hydrogenated as described under Example 5 for the corresponding ethyl analogue to give 3-hydroxy-1-(N-propylcarbamoylmethyl)-pyrid-2-one in 47% yield, m.p. 204°–205° C.; $\nu_{max}$ (nujol) 1560, 1580, 1640, 3050, 3200 $cm^{-1}$, δ($d_6$DMSO) 0.35 (t, 3H), 1.5 (m, 2H), 3.0 (q, 3H), 4.5 (s, 2H), 6.05 (t, 1H) 6.7 (d, 1H), 7.05 (d, 1H), 8.1 (s, 1H), 8.95 (s, 1H).

EXAMPLE 8

The preparation of 3-hydroxy-1-[N-(2'-methylethyl)-carbamoylmethyl]-pyrid-2-one 3-Benzyloxy-1-(succinimido-oxycarbonylmethyl)-pyrid-2-one (1 g), prepared as described under Example 5, is reacted with isopropylamine under substantially similar conditions to those described under Example 5 for the reaction of this compound with ethylamine to give 3-benzyloxy-1-[N-(2'-methylethylcarbamoylmethyl]-pryrid-2-one. This compound is hydrogenated as described under Example 5 for the corresponding ethyl analogue to give 3-hydroxy-1-[N-(2'-methylethyl)-carbamoylmethyl]-pyrid-2-one as a silvery powder in 60% yield, m.p. 238°–241° C.; $\nu_{max}$ (nujol) 1570, 1595, 1650, 3270 $cm^{-1}$; $\delta(d_6DMSO)$ 0.95 (d, 6H), 3.7 (m, 1H), 4.4 (s, 2H), 5.95 (t, 1H) 6.53 (d, 1H), 6.98 (d, 1H), 7.96 (d, 1H), 8.85 (s, 1H).

EXAMPLE 9

The preparation of 1-N-butylcarbamoylmethyl)-3-hydroxypyrid-2-one 3-Benzyloxy-1-(succinimido-oxycarbonylmethyl)-pyrid-2-one (1 g), prepared as described under Example 5, is reacted with n-butylamine under substantially similar conditions to those described under Example 5 for the reaction of this compound with ethylamine to give 3-benzyloxy-1-(N-butylcarbamoylmethyl)-pyrid-2-one. This compound is hydrogenated as described under Example 5 for the corresponding ethyl analogue to give 1-N-butylcarbamoylmethyl)-3-hydroxypyrid-2-one as colourless needles of m.p. 199°–200° C.; $\nu_{max}$ (nujol) 1565, 1595, 1650, 1680, 3100, 3270 $cm^{-1}$; $\delta(d_6DMSO)$, 0.8 (t, 3H), 1.3 (m, 4H), 3.0 (d, 2H), 4.43 (s, 2H) 5.95 (t, 1H) 6.63 (d, 1H), 6.96 (d, 1H), 8.0 (t, 1H), 8.86 (s, 1H)

EXAMPLE 10

The preparation of 1-acetyl-3-hydroxy-2-methylpyrid-4-one

3-Benzyloxy-2-methyl-4-pyrone

3-Hydroxy-2-methyl-4-pyrone (22.2 g) in methanol (225 ml) is added to aqueous sodium hydroxide (25 ml $H_2O$ containing 7.5 g NaOH). Benzyl chloride (25.5 g) is added and the mixture is refluxed for 6 hours and is then allowed to cool overnight. The bulk of the methanol is removed under vacuum and the residue is treated with water (50 ml). The mixture is extracted into dichloromethane (3×25 ml). The extracts are combined, washed with 5% w/v NaOH (2×25 ml), then water (2×25 ml) and dried over magnesium sulphate. Evaporation of the solvent gives crude 3-benzyloxy-2-methyl-4-pyrone (35 g, 92%) which is purified by distillation in nitrogen under reduced pressure to yield a colourless oil (28 g) of b.p. 148° C./0.2 mm.

3-Benzyloxy-2-methylpyrid-4-one

3-Benzyloxy-2-methyl-4-pyrone (20 g), concentrated (s.g. 0.880) ammonia (200 ml) and ethanol (100 ml) are mixed and kept at room temperature for 3 days. The solvent and excess ammonia are then removed by rotary evaporation to yield in oil which on trituration with acetone gives 3-benzyloxy-2-methylpyrid-4-one as white crystals m.p. 162°–163° C.

1-Acetyl-3-benyloxy-2-methylpyrid-4-one 1 3-Benzyloxy-2-methylpyrid-4-one (4 g) is dissolved in dry acetone (100 ml). Acetylbromide (3 g) and triethylamine (2.7 g) are added and the resulting mixture is mechanically stirred overnight. The mixture is then filtered and the filtrate is rotary evaporated to dryness. The residue is dissolved in methylene chloride and washed with dilute hydrochloric acid (pH 3.0), then twice with water, and is dried over $Na_2SO_4$ and rotary evaporated to yield a solid residue. Recrystallisation of this residue from an ethylacetate/hexane mixture gives 1-acetyl-3-benzyloxy-2-methylpyrid-4-one as an oil (3.1 g).

1-Acetyl-3-hydroxy-2-methylpyrid-4-one

1-Acetyl-3-benzyloxy-2-methylpryid-4-one (2 g) is treated with 45% w/v HBr-acetic acid (10 ml) for 1 hour at 100° C. The solution is rotary evaporated to dryness at 70° C. and triturated with an ethyl acetate/methanol (20.1 v/v) mixture. On standing overnight at 4° C. pale brown crystals are deposited (1.2 g) and these are recrystallised from an ethyl acetate/methanol mixture to yield 1-acetyl-3-hydroxy-2-methylpyrid-4-one as white crystals, m.p. 152°–160° C.; $\nu_{max}$ (nujol) 1630, 1680 $cm^{-1}$; $\delta(d_6DMSO)$, 2.2 (s, 3H), 2.5 (s, 3H), 7.25 (d, 1H), 8.15 (d, 1H).

EXAMPLE 11

The preparation of 3-hydroxy-1-(2'-hydroxyethyl)-2methylpyrid-4-one

3-Benzyloxy-1-(2'-hydroxyethyl)-2methylpyrid-4-one

3-Benzyloxy-2-methyl-4-pyrone (4.8 g), prepared as described under Example 10, and 2-hydroxyethylamine (1.22 g) are dissolved in water (220 ml) and ethanol (100 ml) containing sodium hydroxide (2 g) is added. The mixture is stirred at room temperature for 6 days and is then acidified with concentrated hydrochloric acid to pH 2, and evaporated to dryness. The resulting colourless solid is washed with water and extracted into chloroform (2×50 ml). The chloroform extracts are combined, dried over magnesium sulphate, and evaporated to yield 3-benzyloxy-1-(2'-hydroxyethyl)-2-methylpyrid-4-one, as a white solid (3.4 g), m.p. 198°–199° C.

3-Hydroxy-1-(2'-hydroxyethyl)-2-methylpyrid-4-one

3-Benzyloxy-1-(2'-hydroxyethyl)-2-methylpyrid-4-one (2 g) is added to concentrated hydrobromic acid (10 ml) and the mixture is heated on a steam bath for 30 minutes. The resultant product is then recrystallised from water to yield 3-hydroxy-1(2'-hydroxyethyl)-2-methylpyrid-4-one as white crystals (0.8 g), m.p. 164°–165° C.; $\nu_{max}$ (nujol) 1630, 3150, 3350 $cm^{-1}$; $\delta(d_b$ DMSO), 2.5 (s, 3H), 3.7 (t, 2H), 4.35 (t, 2H), 7.25 (3, 1H), 8.15 (d, 1H).

EXAMPLE 12

The preparation of 3-hydroxy-1-(3'-hydroxypropyl)-2-methylpyrid-4-one

3-Benzyloxy-2-methyl-4-pyrone, prepared as described under Example 10, is reacted with 3-hydroxypropylamine under substantially similar conditions to those described under Example 9 for reaction with 2-hydroxyethylamine to give 3-benzyloxy-1-(3'-hydroxypropyl)-2-methylpyrid-4-one. This is deprotected using the procedure described under (I) to give 3-hydroxy-1-(3'-hydroxypropyl)-2-methylpyrid-4-one as white crystals, m.p. 111°–113° C.; $\nu_{max}$ (nujol) 1630, 3150, 3350 $cm^{-1}$, $\delta(d_6$ DMSO) 1.8 (m, 2H), 2.4 (s, 3H, 3.35 (t, 2H), 4.33 (t, 2H), 7.3 (d, 1H), 8.2 (d, 1H).

EXAMPLE 13

The preparation of 3-hydroxy-1-(4'-hydroxybutyl)-2-methylpyrid-4-one

3-Benzyloxy-2-methyl-4-pyrone, prepared as described under Example 10, is reacted with 1-amino-4-hydroxybutane under substantially similar conditions to those described under Example 11 for reaction with 2-hydroxyethylamine to give 3-benzyloxy-1-(4'-hydroxybutyl)-2-methylpyrid-4-one. This is deprotected using the procedure described under (I) to give 3-hydroxy-1-(4'-hydroxybutyl)-2-methylpyrid-4-one as white crystals, m.p. 126°–128° C.; $\nu_{max}$ (nujol) 1630, 3350 $cm^{-1}$; $\delta(d_6$DMSO) 1.5 (m, 4H), 2.45 (s, 3H) 3.35 (t, 2H), 4.30 (t, 2H), 7.25 (d 1H), 8.2 (d, 1H).

EXAMPLE 14

The preparation of 3-hydroxy-1-(5'-hydroxypentyl)-2-methylpyrid-4-one

3-Benzyloxy-2-methyl-4-pyrone, prepared as described under Example 10, is reacted with 1-amino-5-hydroxypentane under substantially similar conditions to those described under Example 11 for reaction with 2-hydroxyethylamine to give 3-benzyloxy-1-(5'-hydroxypentyl)-2-methylpyrid-4-one. This is deprotected using the procedure described under (I) to give 3-hydroxy-1-(5'-hydroxypentyl)-2methylpyrid-4-one as white crystals, m.p. 136°–138° C.; $\nu_{max}$ (nujol) 1625, 3350 $cm^{-1}$: $\delta(d_6$DMSO) 1.3 (m, 6H), 2.40 (s, 3H), 3.25 (t, 2H), 4.20 (t, 2H) 7.20 (d, 1H), 8.15 (d, 1H).

EXAMPLE 15

The preparation of 1-(5'-acetoxypentyl)-3-hydroxy-2-methylpyrid-4-one

3-Hydroxy-1-(5'-hydroxypentyl)-2-methylpyrid-4-one, prepared as described under Example 14, (2 g) is dissolved in glacial acetic acid containing about 1% w/v of hydrogen bromide and the solution is refluxed for 2 hours. The resultant mixture is subjected to rotary evaporation and the residue crystallised from aqueous ethanol to give 1-(5'-acetoxypentyl)-3-hydroxy-2-methylpyrid-4-one in 65% yield. m.p. 132°–133° C., $\nu_{max}$ (nujol) 1520, 1540, 1580, 1635, 1735 $cm^{-1}$ and $\delta(d_6$DMSO), 1.6 (m, 6H), 2.1 (s, 3H), 2.4 (s, 3H), 4.05 (m, 4H), 6.4 (d, 1H), 7.3 (d, 1H).

EXAMPLE 16

The preparation of 1-carboxymethyl-3-hydroxy-2-methylpyrid-4-one

3-Benzyloxy-2-methyl-4-pyrone, prepared as described under Example 10, is reacted with glycine under substantially similar conditions to those described under Example 11 for reaction with 2-hydroxyethylamine to give 3-benzyloxy-1-carboxymethyl-3-hydroxy-2-methylpyrid-4-one, which is deprotected using the procedure described under Example 11 to give 1-carboxymethyl-3-hydroxy-2-methylpyrid-4-one as white crystals, m.p >230° C.; $\nu_{max}$ (nujol) 1625, 1645 $cm^{-1}$; $\delta(d_6$ DMSO) 1.9 (s, 3H), 4.3 (s, 2H), 5.9 (d, 1H), 7.35 (d, 1H).

EXAMPLE 17

The preparation of 2'-carboxyethyl)-3-hydroxy-2-methylpyrid-4-one hydrochloride

3-Benzyloxy-1-(2'-carboxyethyl)-2-methylpyrid-4-one

Benzyloxy-2-methyl-4-pyrone, prepared as described under Example 10, (20 g) and beta-alanine (9 g) dissolved in 3:2 v/v water/ethanol (500 ml) containing NaOH (10 g) to provide a solution with a pH of at least 13. The solution is refluxed for 15 minutes whereupon it turns from a light orange to an intense red colour. The solution is acidified to pH 7.0 and the ethanol is removed by rotary evaporation. The resulting aqueous solution is washed twice with ethylacetate (100 ml). This solution is then subjected to rotary evaporation until the volume is reduced to 100 ml and this reduced volume of solution is acidified to pH 3.0 to give a white precipitate, which is filtered off to give 3-benzyloxy-1-(2'-carboxyethyl)-2-methylpyrid-4-one in 70% yield, m.p. 156°–157° C.

1-(2'-Carboxyethyl)-3-hydroxy-2-methylpyrid-4-one hydrochloride

3-Benzyloxy-1-(2'-carboxyethyl)-2-methylpyrid-4-one is subjected to hydrogenation in aqueous ethanol (1:1 v/v) in the presence of platinum/carbon catalyst (100 mg per gram of pyridone) for 8 hours at 20° C. and atmospheric pressure. Filtration, followed by rotary evaporation of the filtrate, yields a white solid which on recrystallisation from acetone and diethylether gives 1-(2'-carboxyethyl)-3-hydroxy-2-methylpyrid-4-one hydrochloride in 55% yield, m.p. <40° C.: $\nu_{max}$ (nujol) 1590, 1620, 1720 $cm^{-1}$: $\delta(d_6$DMSO) 2.5 (s, 3H), 2.8 (t, 2H), 4.45 (t, 2H), 7.35 (d, 1H,, 8.2 (d, 1H).

EXAMPLE 18

The preparation of 1-(2'-ethoxycarbonylethyl)-3-hydroxy-2-methylpyrid-4-one 1-(2'-Carboxyethyl)-3-hydroxy-2-methylpyrid-4-one hydrochloride (2 g), prepared as described under Example 17, is dissolved in ethanol saturated with hydrogen chloride and the solution is refluxed for 3 hours. Rotary evaporation of the solution yields a white solid which on recrystallisation from ethanol gives 1-(2'-ethoxycarbonylethyl)-3-hydroxy-2-methylpyrid-2-one hydrochloride in 75% yield. m.p. 127°–130° C.; $\nu_{max}$ (nujol) 1530, 1620, 1720 $cm^{-1}$; $\delta(d_6$DMSO) 1.1, (t, 3H) 2.5 (s, 3H), 2.9 (t, 2H), 4.0 (q, 2H), 4.5 (t, 2H), 7.4 (d, 1H), 8.2 (d, 1H).

EXAMPLE 19

The preparation of 3-hydroxy-1-(2'-methoxycarbonylethyl)-2-methylpyrid-4-one 1-(2'-carboxyethyl)-3-hydroxy-2-methylpyrid-4-one hydrochloride (2 g) prepared as described under Example 17, is dissolved in methanol saturated with hydrogen chloride and the solution is refluxed for 3 hours. Rotary evaporation of the solution yields a white solid which on recrystallisation from methanol gives 3-hydroxy-1-(2'-methoxycarbonylethyl)-2-methylpyrid-4-one hydrochloride in 80% yield m.p. 140°–141° C., $\nu_{max}$ 1545, 1595, 1645, 1730, 1750 $cm^{-1}$, $\delta(d_6$DMSO), 2.45 (s, 3H), 2.85 (t, 2H), 3.5 (s, 3H), 4.45 (t, 2H), 7.30 (d, 1H), 8.15 (d, 1H).

EXAMPLE 20

The preparation of 3-hydroxy-1-[2'-(N-propylcarbamoyl)-ethyl]-2-methylpyrid-4-one 3-Benzyloxy-1-[2'-(succinimido-oxycarbonyl)-ethyl]-2-methylpyrid-4-one 3-Benzyloxy-1-(2'-carboxyethyl)-2-methylpyrid-2-one, prepared as described under Example 17, (2.2 g) is dissolved in DMF (25 ml) and to the solution is added N-hydroxysuccinimide (1 g). This solution is cooled and to it is added dicyclohexylcarbodiimide (1.8 g) in DMF (5 ml). The mixture is allowed to stand overnight giving a dark coloured solution and white precipitate. The precipitate is removed by filtration and washed with DMF (3 ml). The solution is rotary evaporated to dryness and triturated with diethylether to give 3-benzyloxy-1-[2'-(succinimido-oxycarbonyl)-ethyl]-2-methylpyrid-4-one hydrochloride as a white solid in 55% yield, m.p. 45°–47° C.

3-Benzyloxy-1-[2'-(N-propylcarbamoyl)-ethyl]-2-methylpyrid-4-one

3-Benzyloxy-1-[2'-(succinimido-oxycarbonyl)-ethyl]-2-methylpyrid-2-one (1 g) is in chloroform (100 ml) and to this solution is added ethylamine in a 2 molar excess. The mixture is allowed to stand for 15 minutes and the N-hydroxysuccinimide liberated by the reaction is then extracted with 1M $NaHCO_3$ solution (2×25 ml). The organic layer is dried over $Na_2SO_4$, filtered and evaporated to dryness to give 3-benzyloxy-1-[2'-(N-propylcarbamoyl)-ethyl]-2-methylpyrid-4-one as a white solid in 40% yield, m.p. 146°–147° C.

3-Hydroxy-1-[2'-(N-propylcarboamoyl)-ethyl]-2-methylpyrid-4-one

3-Benzyloxy-1-[2'-N-propylcarbamoyl)-ethyl]-2-methylpyrid-4-one (5 g) is dissolved in 50:50 v/v aqueous ethanol. Platinum/carbon catalyst (100 mg) is added and the solution is hydrogenated at 20° C. and atmospheric pressure for 8 hours. The mixture is filtered, the filtrate subjected to rotary evaporation and the resulting residue recrystallised from ethanol to give 3-hydroxyy-1-[2'-(N-propylcarbamoyl)-ethyl]-pyrid 4-one, m.p. 113°–114 C., $\nu_{max}$ (nujol) 1505, 1550, 1570, 1630, 1705, 3080, 3200 $cm^{-1}$. $\delta(d_6DMSO)$ 0.6 (t, 3H), 1.2 (sextuplet, 2H), 2.5 (s, 3H), 2.6 2.8 (overlapping t and q, 4H), 4.5 (t, 2H), 7.2 (d, 1H), 8.1 (overlapping d and t, 2H).

EXAMPLE 21

The preparation of 1-(2'-aminoethyl)-3-hydroxy-2-methylpyrid-4-one hydrochloride 3-Benzyloxy-2-methyl-4-pyrone prepared as described under Example 4, (4 g), and ethylene diamine (1.5 g) are heated together under reflux in water (50 ml) and ethanol (17 ml) for 1 hour. The solvent is removed by rotary evaporation and the solid residue is heated at 80° C. with concentrated hydrochloric acid (50 ml) for 30 minutes. Excess acid is removed by rotary evaporation at 80° C. and the residue is slurried with acetone, yielding a pale brown solid (2.2 g). Recrystallisation from ethanol, containing a trace of hydrochloric acid yields 1-(2'-aminoethyl)-3-hydroxy-2-methylpyrid-4-one hydrochloride as white crystals, m.p. 280° C. (with decomposition); $\nu_{max}$ (nujol) 1620, 3150 $cm^{-1}$; $\delta(D_2O)$ 2.5 (s, 3H), 3.5 (t, 2H) 4.5 (t, 2H), 7.1 (d, 1H), 8.1 (d, 1H).

EXAMPLE 22

The preparation of 3-hydroxy-6-hydroxymethyl-1-methylpyrid-4-one

3-Benzyloxy-6-benzyloxymethylpyrid-4-one

Kojic acid (3-hydroxy-6-hydroxymethylpyrid-4-one) (11.5 g) in methanol (90 ml) is added to an aqueous solution of sodium hydroxide (3 g in 10 ml). Benzylchloride (10.2 g) is added and the mixture is stirred and refluxed for 6 hours. On cooling, crystals are obtained which are recrystallisated from methanol to give 3-benzyloxy-6-benzyloxymethylpyrid-4-one as white crystals (10 g), m.p. 103°–131° C.; $\delta(CDCl_3)$ 4.25 (s, 2H), 4.99 (s, 2H), 6.25 (s, 1H), 7.3 (s, 5H), 8.1 (s, 1H).

3-Hydroxy-6-hydroxymethyl-1-methylpyrid-4-one

3-Benzyloxy-6-benzyloxypyrid-4-one (5.0 g) and methylamine hydrochloride (1.56 g) are dissolved in aqueous ethanol (300 ml of 2:1 $H_2O$—$C_2H_5OH$ by volume containing 2 g of sodium hydroxide). The reaction mixture is stirred at room temperature for 6 days and then acidified with concentrated HCl to pH 2.0. The yellow mixture is evaporated to dryness and the resulting solid residue is heated under reflux with concentrated HCl (50 ml) for 30 minutes. The product is rotary evaporated to dryness yielding a brown residue which on trituration with acetone forms crystals. Recrystallisation of these from ethanol gives 3-hydroxymethyl-1-methylpyrid-4-one in 15% yield, m.p. 185°–186° C.; $\delta(d_6$ DMSO), 3.9 (s, 3H), 4.6 (s, 2H), 7.4 (s, 1H), 8.3 (s, 1H).

EXAMPLE 23

The preparation of 1-ethyl-3-hydroxy-6-hydroxy-methylpyrid-4-one

3-Benzyloxy-6-benzyloxypyrid-4-one, prepared as described under Example 22, is reacted with ethylamine hydrochloride under substantially similar conditions to those described under Example 22 for reaction with methylamine hydrochloride to give 1-ethyl-3-hydroxy-6-hydroxymethylpyrid-4-one as white crystals, m.p. 143°–145° C.; $\delta(d_6$ DMSO) 1.1 (t, 3H) 4.0 (q, 2H), 4.3 (s, 2H) 7.2 (s, 1H), 8.1 (s, 1H).

EXAMPLE 24

The preparation of 1-(2'-aminoethyl)-3-hydroxypyrid-4-one

3-Benzyloxy-4-pyrone is prepared from 3-hydroxy-4-pyrone as described by Spenser et al, Canadian Journal of Chemistry, 1962, 40, 1377 and has m.p. 82°–85° C. A mixture of this compound (1 g) and ethylenediamime (0.37 g) in water (12 ml) is heated under reflux for 1 hour. The reaction mixture is evaporated to dryness and the residue is treated with concentrated hydrochloric acid (12 ml) and the mixture is heated on a steam bath for 30 minutes. The excess acid and water are evaporated under reduced pressure to give a solid brown residue. This is slurried in acetone, then filtered off and recrystallised from ethanol containing a little concentrated hydrochloric acid to give 1-(2'-aminoethyl-3-hydroxypyrid-4-one in 34% yield as colourless needles, m.p. 264°–266° C., $\nu_{max}$ (nujol) 1050, 1540, 1600, 1635 $cm^{-1}$, $\delta(d_6DMSO)$, 2.85 (t, 2H), 4.35 (t, 2H), 7.1 (d, 1H), 8.1 (m, 2H).

EXAMPLE 25

Partition data on 3-hydroxypyrid-2-and-4-ones and their iron complexes

The partition coefficient $K_{part}$, being the ratio (concentration of compound in n-octanol)/(concentration of compound in aqueous phase) on partition between n-octanol and aqueous tris hydrochloride (20 mM, pH 7.4), is measured by spectrophotometry at 20° C. for various of the compounds of the previous Examples and for their 3:1 iron(III) complexes (at $10^{-4}$M) by spectrophotometry. The solutions of the complexes are either produced by dissolving the pre-formed complex in the aqueous tris hydrochloride or are prepared in situ in the buffer by the admixture of a 3:1 molar ratio of the pyridone and ferric chloride, the pH thereafter being readjusted to 7.4 if necessary (the same product will be obtained in the buffer solution irrespective of whether the pyridone used is in a salt form or not). Acid washed glassware is used throughout and, following mixing of 5 ml of the $10^{-4}$M aqueous solution with 5 ml n-octanol for 1 minute, the aqueous n-octanol mixture is centrifuged at 1,000 g for 30 seconds. The two resulting phases are separated for a concentration determination by spectrophotometry on each. For the free hydroxypyridones, the range 220–340 nm is used for concentration determinations whilst for the iron complexes, the range 340–640 nm is used.

Values typical of those obtained are shown in Table 1.

TABLE 1

Partition coefficients

| Compound | Partition coefficient $K_{part}$ Free compound | Iron complex [$FE^{///-}$ (compound)$_3$] |
|---|---|---|
| 1-acetyl-3-hydroxypyrid-2-one | 0.55 | 0.24 |
| 1-ethoxycarbonylmethyl-3-hydroxyprid-2-one | 0.5 | 0.19 |
| 3-hydroxy-1-methoxycarbonyl-methylpyrid-2-one | 0.2 | 0.02 |
| 1-(N-ethylcarbamoylmethyl-3-hydroxypyrid-2-one | 0.12 | 0.01 |
| 3-hydroxy-1-(N-methylcarbamoyl-methyl)-pyrid-2-one | 0.06 | 0.005 |
| 3-hydroxy-1(N-propylcarbamoyl-methyl)-pyrid-2-one | 0.35 | 0.14 |
| 3-hydroxy-1-[N-(2'-methylethyl) carbamoylmethyl]-pyrid-2-one | 0.34 | 0.15 |
| 1-(N-butylcarbamoylmethyl)-3-hydroxypyrid-2-one | 1.89 | 5.12 |
| 3-hydroxy-1-(2'-hydroxyethyl) 2-methylpyrid-4-one | <0.002 | <0.002 |
| 3-hydroxy-1-(3'-hydroxypropyl)-2-methylpyrid-4-one | 0.10 | 0.06 |
| 3-hydroxy-1-(4'-hydroxybutyl)-2-methylpyrid-4-one | 0.14 | 0.03 |
| 3-hydroxy-1-(5'-hydroxypentyl-2-methylpyrid-4-one | 0.28 | 0.04 |
| 1-(5'-acetoxypentyl-3-hydroxy-2-methylpyrid-4-one | 0.45 | 0.03 |
| 1-carboxymethyl-3-hydroxy-2-methylpyrid-4-one | <0.002 | <0.002 |
| 1-(2'-carboxyethyl)-3-hydroxy-2-methylpyrid-4-one | 0.45 | 0.03 |
| 1-(2'-aminoethyl-3-hydroxy-2-methylpyrid-4-one | <0.002 | <0.002 |
| 3-hydroxy-6-hydroxymethyl-1-methylpyrid-4-one | 0.03 | 0.01 |
| 1-ethyl-3-hydroxy-6-hydroxymethyl pyrid-4-one | 0.06 | 0.07 |

EXAMPLE 26

In vitro tests of iron binding capacity

The 3-hydroxypyridones used in this Example were prepared as described in various of the previous Examples.

(1) Mobilisation of iron from ferritin

Horse spleen ferritin (Sigma) was used without further purification and its iron content was estimated spectrophotometrically at 420 nm. The ferritin solution in phosphate buffered saline (Dulbecco-OXOID, $10^{-6}$M, pH 7.4) was enclosed in a Visking dialysis tube and dialysed against a $3\times10^{-3}$M buffered solution of one of various pyridones as indicate in Table 2. The absorption spectrum of the resulting iron (III) complex in the dialysis solution was recorded after 6 and 24 hours. For comparative purposes, the procedure was repeated using a blank control.

The results are shown in Table 2 where the percentage of ferritin-bound iron removed by the compound under test is shown. For comparative purposes, results reported in the literature for similar tests with $1\times10^{-3}$M desferrioxaamine (Crichton et al, J. Inorganic Biochem., 1980, 13, 305) and with $6\times10^{-3}$M LICAMS (Tufano et al. Biochem. Biophys. Acta, 1981, 668, 420) are also given in the Table. It will be seen that the pyridone compounds are able to remove iron effectively from ferritin in contrast with desferrioxamine and LICAMS (although the latter will remove iron in the presence of ascorbic acid such a mixture is very difficult to manage clinically). These results shown in Table 2 have been confirmed by separating apoferritin (in admixture with ferritin) and the particular hydroxypyridone iron (III) complex from the reaction product in each case by chromatography on Sephadex G10.

TABLE 2

Removal of iron from ferritin

| Compound | Percentage of iron removed 6 hours | 24 hours |
|---|---|---|
| Control | 0 | 0 |
| 1-acetyl-3-hydroxypyrid-2-one | 15 | 24 |
| 3-hydroxy-1-(2'-hydroxyethyl)-2-methylpyrid-4-one | 31 | 49 |
| 1-carboxymethyl-3-hyroxy-2-methylpyrid-4-one | <5 | <5 |
| 3-hydroxy-1-(2'-methoxycarbonylethyl)-2-methylpyrid-4-one | 22 | 45 |
| 1-(2'-aminoethyl)-3-hydroxy-2-methylpyrid-4-one | 28 | 61 |
| 3-hydroxy-6-hydroxymethyl-1-methylpyrid-4-one | 25 | 49 |
| Desferrioxamine (1 mM) | 1.5 | — |
| LICAMS (6 mM) | 0 | — |
| LICAMS (6 mM + 12 mM ascorbic acid) | 7 | — |

(2) Mobilisation of iron from transferrin

Human transferrin (Sigma) was loaded with iron (III) by the method of Bates and Schlaback, J. Biol. Chem. (1973) 248, 3228. $^{59}$ Iron (III) transferrin ($10^{-5}$M) was incubated with a $4\times10^{-3}$M solution in tris HCl (0.1M, pH 7.4) of one or various pyridones as indicated in Table 3 for periods of 4 hours and 18 hours. The solution was then dialysed against phosphate buffered saline for 24 hours. The $^{59}$Fe remaining in the dialysis tube was then recorded. For comparative purposes, this procedure was repeated with desforrioxamine using incubation for both 4 hours and 18 hours and with EDTA using incubation for 4 hours only.

The results are shown in Table 3 in terms of the percentage of transferrin bound iron removed by the compound under test. It will be seen that the pyrid-4-one compounds are very effective at iron removal, as compared with desferrioxamine or EDTA, after only 4 hours. Although the efficiency at iron removal of the pyrid-2-one compounds is only at a similar level to that of desferrioxamine and EDTA after 4 hours, it increases markedly after 18 hours whereas the level for desferrioxamine at 18 hours is substantially similar to that at 4 hours.

The results shown in Table 3 have been confirmed by separating apotransferrin (in admixture with transferrin) and the particular hydroxypyridone iron complex from the reaction product in each case by chromatography on Sephadex G10.

TABLE 3

Removal of iron from transferrin

| Compound | Percentage of iron removed 4 hours | 18 hours |
|---|---|---|
| 1-acetyl-3-hydroxypyrid-2-one | 15 | 30 |
| 1-carboxymethyl-3-hyroxypyrid-2-one | 35 | — |
| 3-hydroxy-1-methoxycarbonylmethyl-pyrid-2-one | 18 | — |
| 3-hydroxy-1-[N-(2'-methylethyl)-carbamoylmethyl]-pyrid-2-one | 41 | — |
| 3-hyrdroxy-1-(2'-hydroxyethyl)-2-methylpyrid-4-one | 94 | 96 |
| 1-carboxymethyl-3-hydroxy-2-methylpyrid-4-one | 82 | 88 |
| 1-(2'-aminoethyl)-3-hydroxy 2-methylpyrid-4-one | 97 | 98 |
| 3-hydroxy-6-hydroxymethyl-1-methylpyrid-4-one | 93 | 97 |
| Desferroxamine | 17 | 22 |
| EDTA | 27 | 67 |

The results are shown in Table 4, being given on the basis of the control representing 100% excretion, and illustrate the particular advantage of the pyridones as compared with desferrioxamine for oral administration the levels of iron excreted on intragastric administration being higher for all the pyridones tested than for desferrioxamine. It should be mentioned that the large standard deviation (SD) values are somewhat misleading as uniformly positive results can yield high SDs which might be taken to suggest that the results are not significantly different from zero. However, this is not the case here, the large SD values being a consequence of the large range among the positive responses.

TABLE 4

Excretion of iron in vivo

| Compound | Intraperitoneal Administration: Number of Mice | Excretion of $^{59}Fe$ ± SD percent | Intragastric Administration: Number of Mice | Excretion of $^{59}Fe$ ± SD percent |
|---|---|---|---|---|
| Control | 12 | 100 ± 10 | — | — |
| 1-acetyl-3-hydroxypyrid-2-one | 8 | 136 ± 33 | 8 | 137 ± 45 |
| 1-ethyoxycarbonylmethyl-3-hydroxypyrid-2-one | 12 | 90 ± 11 | 12 | 92 ± 13 |
| 3-hydroxy-1-(2'-hydroxyethyl)-2-methylpyrid-4-one | 11 | 170 ± 49 | 11 | |
| 3-hydroxy-1-(5'-hydroxypentyl)-2-methylpyrid-4-one | 9 | 149 ± 59 | 9 | 111 ± 22 |
| 1-carboxymethyl-3-hydroxy-2-methylpyrid-4-one | 6 | 96 ± 11 | 5 | 99 ± 10 |
| 1-(2'-aminoethyl)-3-hydroxy-2-methylpyrid-4-one | 12 | 115 ± 16 | 12 | 100 ± 14 |
| Desferrioxamine | 5 | 414 ± 100 | 4 | 88 ± 17 |

EXAMPLE 27

In vivo tests of iron binding capacity

The 3-hydroxypyridones used in this Example were prepared as described in various of the previous Examples.

Mice were injected intraperitoneally with iron dextran (2 mg) at weekly intervals over a four week period Two weeks after the final injection, the mice were injected via the tail vein with $^{59}Fe$ lactoferrin (human lactoferrin, 1 mg per injection 2 μCi). The mice were then caged individually. After a ten day period, 1-acetyl-3-hydroxypyrid-2-one was administered to groups of 8 mice at 10 mg per mouse either intraperitoneally or intragastrically (in each case 3 of the mice received only one dose whilst 5 received 2 doses at a 24 hour interval. The excretion of iron was recorded at either 12 or 24 hourly intervals over a three day period before and a two day period after administration of the compound. For comparative purposes, the procedure was repeated with a blank control and with desferrioxamine, also at 10 mg per mouse (the intraperitoneally treated mice receving one dose of desferrioxamine and the intragastrically treated mice two doses at a 24 hour interval.

We claim:

1. A method for the treatment of a patient having a toxic concentration of a metal selected from the group consisting of iron, copper, and aluminum in the body of said patient which comprises administering to said patient a therapeutic amount of a 3-hydroxypyrid-2-one or 3-hydroxypyrid-4-one in which the hydrogen atom atached to the nitrogen atom is replaced by an aliphatic acyl group, an aliphatic hydrocarbon group, or an aliphatic hydrocarbon group substituted by one or more substituents selected from aliphatic acyl, alkoxy, aliphatic amide, aliphatic ester, halogen and hydroxy groups, and wherein one or more of the hydrogen atoms attached to ring carbon atoms can be replaced by an aliphatic acyl, alkoxy, aliphatic amide, aliphatic ester, halogen or hydroxy group, an aliphatic hydrocarbon group, or an aliphatic hydrocarbon group substituted by an alkoxy, aliphatic ester, halogen or hydroxy group, but excluding compounds in which said replacement of hydrogen atoms is effected only by aliphatic hydrocarbon groups, or a salt thereof containing a physiologically acceptable cation.

2. The method of claim 1 wherein said metal is iron or aluminum.

3. The method according to claim 1, in which the metal is iron.

4. The method according to claim 3, in which the 3-hydroxypyridone is substituted only on the nitrogen atom or is substituted on the nitrogen atom and on one of the ring carbon atoms.

5. The method according to claim 4, in which the ring carbon atom substituent is a $C_{1-4}$ aliphatic hydrocarbon group.

6. The method according to claim 5, in which the nitrogen atom is substituted by a $C_{2-5}$ alkylcarbonyl group or by a $C_{1-6}$ aliphatic hydrocarbon group substituted by a single substituent selected from $C_{2-5}$ alkylcarbonyl, $C_{1-4}$ alkoxy, halogen, hydroxy, $C_{1-4}$ alkyl ester groups and unsubstituted or $C_{1-4}$ alkyl mono- or di-substituted amide groups.

7. The method according to claim 3, in which the 3-hydroxypyridone is 3-hydroxypyrid-2-one, 3-hydroxypyrid-4-one, 3-hydroxy-2-methylpyrid-4-one, 3-hydroxy-6-methylpyrid-4-one or -3-hydroxy-2,6-dimethylpyrid-4-one with the hydrogen atom attached to the nitrogen atom replaced by an aliphatic acyl group —$COR_1$, an aliphatic hydrocarbon group —$(CH_2)_n$— carrying a terminal substituent group —$COR_1$, —$COXR_1$, —$SO_2XR_1$, —$XCOR_1$ or —$XSO_2R_1$, or an aliphatic hydrocarbon group —$(CH_2)_m$—carrying a terminal substituent group —OH, wherein $R_1$ is a $C_{1-4}$ acyclic alkyl group, X is an oxy or imino group, n is an integer from 1 to 4 and m is an integer from 3 to 6.

8. A pharmaceutical composition comprising: (a) a 3-hydroxypyrid-2-one or 3-hydroxypyrid-4-one in which the hydrogen atom attached to the nitrogen atom is replaced by an aliphatic acyl group, an aliphatic hydrocarbon group, or an aliphatic hydrocarbon group substituted by one or more substituents selected from aliphatic acyl, alkoxy, aliphatic amide, aliphatic ester, halogen and hydroxy groups, and wherein one or more of the hydrogen atoms attached to ring carbon atoms can be replaced by an aliphatic acyl, alkoxy, aliphatic amide, aliphatic ester, halogen or hydroxy group, an aliphatic hydrocarbon group, or an aliphatic hydrocarbon group substituted by an alkoxy, aliphatic ester, halogen or hydroxy group, but excluding compounds in which said replacement of hydrogen atoms is effected only by aliphatic hydrocarbon groups, or a salt thereof containing a physiologically acceptable cation; and (b) a physiologically acceptable solid carrier.

9. A pharmaceutical composition comprising: (a) a 3-hydroxypyrid-2-one or 3-hydroxypyrid-4-one in which the hydrogen atom attached to the nitrogen atom is replaced by an aliphatic acyl group, an aliphatic hydrocarbon group or an aliphatic hydrocarbon group substituted by one or more substituents selected from aliphatic acyl, alkoxy, aliphatic amide, aliphatic ester, halogen and hydroxy groups, and wherein one or more of the hydrogen atoms attached to ring carbon atoms can be replaced by an aliphatic acyl, alkoxy, aliphatic amide, aliphatic ester, halogen or hydroxy group, an aliphatic hydrocarbon group, or an aliphatic hydrocarbon group substituted by an alkoxy, aliphatic ester, halogen or hydroxy group, but excluding compounds in which said replacement of hydrogen atoms is effected only by aliphatic hydrocarbon groups, or a salt thereof containing a physiologically acceptable cation; and (b) a physiologically acceptable diluent which is sterile and pyrogen-free.

10. A pharmaceutical composition comprising: (a) a 3-hydroxypyrid-2-one or 3-hydroxypyrid-4-one in which the hydrogen atom attached to the nitrogen atom is replaced by in aliphatic acyl group, or an aliphatic hydrocarbon group substituted by one or more substituents selected from aliphatic acyl, alkoxy, aliphatic amide, aliphatic ester, halogen and hydroxy groups, and wherein one or more of the hydrogen atoms attached to ring carbon atoms can be replaced by an aliphatic hydrocarbon group, but excluding the specific compounds 3-hydroxy-1-(2'-hydroxyethyl)-2-methylpyrid-4-one and 1-methoxycarbonylmethyl-3-hydroxy-2-methylpyrid-4-one, or a salt thereof containing a physiologically acceptable cation; and (b) a physiologically acceptable diluent or carrier.

11. The pharmaceutical composition according to claim 10, in which the nitrogen atom is substituted by a $C_{2-5}$ alkylcarbonyl group or by a $C_{1-6}$ aliphatic hydrocarbon group substituted by a single substituent selected from $C_{2-5}$ alkylcarbonyl, $C_{1-4}$ alkoxy, halogen, hydroxy, $C_{1-4}$ alkyl ester groups and unsubstituted or $C_{1-4}$ alkyl mono- or di-substituted amide groups, and wherein one of the ring carbon atoms can be substituted by a $C_{1-4}$ aliphatic hydrocarbon group.

12. The pharmaceutical composition according to claims 10, in which the 3-hydroxypyridone is 3-hydroxypyrid-2-one, 3-hydroxypyrid-4-one, 3-hydroxy-2-methylpyrid-4-one, 3-hydroxy-6-methylpyrid-4-one or 3-hydroxy-2,6-dimethylpyrid-4-one with the hydrogen atom attached to the nitrogen atom replaced by an aliphatic acyl group —$COR_1$, an aliphatic hydrocarbon group —$(CH_2)_n$—carrying a terminal substituent group —$COR_1$, —$COXR_1$, —$SO_2XR_1$, —$XCOR_1$ or —$XSO_2R_1$, or an aliphatic hydrocarbon group —$(CH_2)_m$—carrying a terminal substituent group —OH, wherein $R_1$ is a $C_{1-4}$ acyclic alkyl group, X is an oxy or imino group, n is an integer from 1 to 4 and m is an integer from 3 to 6.

13. The pharmaceutical composition according to claim 10, in which the 3-hydroxypyridone is in the form of the free compound rather than in the form of a salt thereof.

14. The pharmaceutical composition according to claim 10, in which the carrier is a physiologically acceptable solid carrier.

15. The pharmaceutical composition according to claim 14, in tablet or capsule form.

16. The pharmaceutical composition according to claim 10 which comprises water and/or an organic solvent as the physiologically acceptable diluent and which has the form of a solution, suspension or emulsion.

17. The pharmaceutical composition according to claim 16 in sterile injectable form.

18. The pharmaceutical composition according to claim, 10 in unit dosage form.

19. A compound being 3-hydroxypyrid-2-one [or 3-hydroxypyrid-4-one] in which the hydrogen atom attached to the nitrogen atom is replaced by an aliphatic acyl group[, an aliphatic hydrocarbon group,] or an aliphatic hydrocarbon group substituted by one or more substituents selected from aliphatic acyl, alkoxy, aliphatic amide, aliphatic ester, halogen and hydroxy groups, *or 3-hydroxypyrid-4-one in which the hydrogen atom attached to the nitrogen atom is replaced by an aliphatic acyl group, an aliphatic hydrocarbon group, or an aliphatic hydrocarbon group substituted by one or more substituents selected from aliphatic acyl alkoxy aliphatic amide, aliphatic ester, halogen and hydroxy groups*, and wherein *in said 3-hydroxypyrid-2-one or 3-hydroxypyrid-4-one* one or more of the hydrogen atoms attached to ring carbon atoms can be replaced by an aliphatic acyl, alkoxy, aliphatic amide, aliphatic ester, [halogen] or hydroxy group, an aliphatic hydrocarbon group, or an aliphatic hydrocarbon group substituted by an alkoxy, aliphatic ester, halogen or hydroxy group, but excluding compounds in which said replacement of hydrogen atoms is effected only by aliphatic hydrocarbon groups and also the specific compounds 2-chloromethyl-3-hydroxy-1-methylpyrid-4-one, 3-hydroxy-2-hydroxymethyl-1-methylpyrid-4-one, 1-ethyl-3-hydroxy-2-hydroxymethylpyrid-4-one, 3-hydroxy-1-(2'-hydroxymethyl)-2-methylpyrid-4-one and 1-methoxycarbonylmethyl-3-hydroxy-2-methylpyrid-4-one, or a salt thereof containing a physiologically acceptable cation.

20. The compound according to claim 19, in which the 3-hydroxypyridone is substituted only on the nitrogen atom or is substituted on the nitrogen atom and on one of the ring carbon atoms.

21. The compound according to claim 20 in which the ring carbon atom substituent is a $C_{1-4}$ aliphatic hydrocarbon group.

22. The compound according to claim 19, being 3-hydroxypyrid-2-one, 3-hydroxypyrid-4-one, or a 2-alkyl-3-hydroxypyrid-4-one, 6-alkyl-3-hydroxypyrid-4-one, or 2,6-dialkyl-3-hydroxypyrid-4-one with the hydrogen atom attached to the nitrogen atom replaced by a $C_{2-5}$ alkylcarbonyl group or by a $C_{1-6}$ aliphatic hydrocarbon group substituted by a single substituent selected from $C_{2-5}$ alkylcarbonyl, $C_{1-4}$ alkoxy, halogen, hydroxy, $C_{1-4}$ alkyl ester groups and unsubstituted or $C_{1-4}$ alkyl mono- or di-substituted amide groups.

23. The compound according to claim 22, in which the alkyl groups at the 2-, 6- or 2- and 6-positions of the 3-hydroxypyridone are $C_{1-3}$ acyclic groups.

24. The compound according to claim 19, being 3-hydroxypyrid-2-one, 3-hydroxypyrid-4-one, 2-methyl-3-hydroxypyrid-4-one, 6-methyl-3-hydroxypyrid-4-one or 2,6-dimethyl-3-hydroxypyrid-4-one with the hydrogen atom attached to the nitrogen atom replaced by an aliphatic acyl group $—COR_1$, an aliphatic hydrocarbon group $—(CH_2)_n—$ carrying a terminal substituent group $—COR_1$, $—COXR_1$, $—SO_2XR_1$, $—XCOR_1$ or $—XSO_2R_1$, or an aliphatic hydrocarbon group $—(CH_2)_m—$ carrying a terminal substituent group —OH, wherein $R_1$ is a $C_{1-4}$ aliphatic hydrocarbon group, X is an oxy or imino group, n is an integer from 1 to 6, and m is an integer from 2 to 6.

25. The compound according to claim 24, in which the nitrogen atom is substituted by a group $—(CH_2)_n—COXR_1$ wherein $—(CH_2)_n—$and $R_1$ together contain 3 to 7 carbon atoms.

26. The compound according to claim 24, in which $R_1$ is a $C_{1-4}$ acyclic alkyl group, n is an integer from 1 to 4 and m is an integer from 3 to 6.

27. The compound according to claim 19 being 3-hydroxypyrid-2-one N-substituted by a group $—(CH_2)_nCOXR_1$ or 3-hydroxy-2-methylpyrid-4-one N-substituted by a group $—(CH_2)_nCOXR_1$ or $—(CH_2)_mXH$ wherein X is an oxy group, $R_1$ is an acyclic alkyl group of 1 to 4 carbon atoms, n is an integer from 1 to 4 with the number of carbon atoms in $—(CH_2)_n—$and $R_1$ together being 3 to 7 carbon atoms, and m is an integer from 3 to 6.

28. The compound according to claim 19, in which the hydrogen atom attached to the nitrogen atom is replaced by an aliphatic hydrocarbon group and the hydrogen atom attached to the ring carbon atom at the 6-position is replaced by an alkoxymethyl, halomethyl or hydroxymethtyl group.

29. The compound according to claim 28, in which the aliphatic hydrocarbon group is an acyclic alkyl group of 1 to 4 carbon atoms.

30. A 3-hydroxypyrid-2-one or 3-hydroxypyrid-4-one in which the hydrogen atom attached to the nitrogen atom is replaced by an aliphatic acyl group, an aliphatic hydrocarbon group, or an aliphatic hydrocarbon group substituted by one or more substituents [by one or more substituent] selected from aliphatic acyl, alkoxy, aliphatic amide, aliphatic ester, halogen and hydroxy groups, and wherein one or more of the hydrogen atoms attached to ring carbon atoms can be replaced by an aliphatic acyl, alkoxy, aliphatic amide, aliphatic ester, halogen or hydroxy group, an aliphatic hydrocarbon group, or an aliphatic hydrocarbon group substituted by an alkoxy, aliphatic ester, halogen or hydroxy group, at least one hydrogen atom attached to either a nitrogen or a carbon atom being replaced by an aliphatic hydrocarbon group substituted by an aliphatic amide group, or by an aliphatic amide group, respectively, or a salt thereof containing a physiologically acceptable cation, the 3-hydroxypyridone or salt thereof being linked to a support material through said amide group.

31. A 3-hydroxypryd-2-one or 3-hydroxypyrid-4-one according to claim 30, in which the hydrogen atom attached to the nitrogen atom is replaced by a $C_{1-8}$ aliphatic hydrocarbon group substituted by an aliphatic amide group and wherein one or more of the hydrogen atoms attached to ring carbon atoms can be replaced by a $C_{1-6}$ aliphatic hydrocarbon group.

32. A method for the treatment of a patient having a toxic concentration of a metal selected from the group consisting of iron, copper, and aluminum in the body which comprises contacting the patient's blood outside the body with a 3-hydroxypyrid-2-one or 3-hydroxypyrid-4-one in which the hydrogen atom attached to the nitrogen atom is replaced by an aliphatic acyl group, an aliphatic hydrocarbon group, or an aliphatic hydrocarbon group substituted by one or more substituents selected from aliphatic acyl, alkoxy, aliphatic amide, aliphatic ester, halogen and hydroxy groups, and wherein one or more of the halogen atoms attached to ring carbon atoms can be replaced by an aliphatic acyl, alkoxy, aliphatic amide, aliphatic ester, halogen or hydroxy group, an aliphatic hydrocarbon group, or an aliphatic hydrocarbon group substituted by an alkoxy, aliphatic ester, halogen or hydroxy group, at least one hydrogen atom attached to either a nitrogen or a carbon atom being replaced by in aliphatic hydrocarbon group substituted by an aliphatic amide group, or by an aliphatic amide group, respectively, or a salt thereof containing a physiologically acceptable cation, the 3-hydroxypyridone or salt thereof being linked to a support material through said amide group.

33. The method according to claim 32, in which the metal is aluminum.

34. The method according to claim 32, which employs a 3-hydroxypyridone in which the hydrogen atom attached to the nitrogen atom is replaced by a $C_{1-8}$ aliphatic hydrocarbon group substituted by an aliphatic amide group and wherein one or more of the hydrogen atoms attached to ring carbon atoms can be replaced by a $C_{1-6}$ aliphatic hydrocarbon group.

*35. The method according to claim 1, in which the 3-hydroxypyridone is a 3-hydroxypyrid-4-one.*

*36. The method according to claim 35, in which the 3-hydroxypyrid-4-one is substituted at the 2-position.*

*37. The method according to claim 35, in which the 3-hydroxypyrid-4-one is an N-substituted 2-alkyl-3-hydroxypyrid-4-one, 6-alkyl-3-hydroxypyrid-4-one or 2,6-dialkyl-3-hydroxypyrid-4-one wherein the alkyl group is methyl, ethyl, propyl or isopropyl.*

*38. The method according to claim 1, in which the hydrogen atom attached to the nitrogen atom is replaced by a group $—(CH_2)_mOH$ wherein m is an integer of 2 to 4.*

*39. The method according to claim 35, in which the nitrogen atom of the 3-hydroxypyrid-4-one is substituted by*

*a group —$(CH_2)_mOH$ wherein m is an integer of 2 to 4, and the ring carbon atoms are either unsubstituted or the ring carbon atom at the 2-position is substituted by a methyl or ethyl group.*

*40. The method according to claim 1, in which the hydrogen atom attached to the nitrogen atom is replaced by a $C_1$–$C_6$ aliphatic hydrocarbon group substituted by a formyloxy, ($C_1$–$C_4$ alkyl)-carbonyloxy, ($C_1$–$C_4$ alkyl)-oxycarbonyl, ($C_1$–$C_4$ alkyl)-sulphonyloxy or ($C_1$–$C_4$ alkyl)-oxysulphonyl group.*

*41. The method according to claim 1, in which the 3-hydroxypyridone is 3-hydroxy-1-(2'-hydroxethyl)-2-methylpyrid-4-one or a salt thereof.*

*42. The method according to claim 1, in which the 3-hydroxypyridone is 3-hydroxy-1-(3'-hydroxypropyl)-2-methylpyrid-4-one or a salt thereof.*

*43. The pharmaceutical composition according to claim 10, in which the 3-hydroxypyridone is a 3-hydroxypyrid-4-one.*

*44. The pharmaceutical composition according to claim 43, in which the 3-hydroxypyrid-4-one is substituted at the 2-position.*

*45. The pharmaceutical composition according to claim 43, in which the 3-hydroxypyrid-4-one is an N-substituted 2-alkyl-3-hydroxypyrid-4-one, 6-alkyl-3-hydroxypyrid-4-one or 2,6-dialkyl-3-hydroxypyrid-4-one wherein the alkyl group is methyl, ethyl, propyl or isopropyl.*

*46. The pharmaceutical composition according to claim 10, in which the hydrogen atom attached to the nitrogen atom is replaced by a group —$(CH_2)_mOH$ wherein m is an integer of 2 to 4.*

*47. The pharmaceutical composition according to claim 43, in which the nitrogen atom of the 3-hydroxypyrid-4-one is substituted by a group —$(CH_2)_mOH$ wherein m is an integer of 2 to 4, and the ring carbon atoms are either unsubstituted or the ring carbon atom at the 2-position is substituted by a methyl or ethyl group.*

*48. The pharmaceutical composition according to claim 10, in which the hydrogen atom attached to the nitrogen atom is replaced by a $C_1$–$C_6$ aliphatic hydrocarbon group substituted by a formyloxy, ($C_1$–$C_4$ alkyl)-carbonyloxy, ($C_1$–$C_4$ alkyl)-oxycarbonyl, ($C_1$–$C_4$ alkyl)-sulphonyloxy or ($C_1$–$C_4$ alkyl)-oxysulphonyl group.*

*49. The pharmaceutical composition according to claim 8, in which the 3-hydroxypyridone is 3-hydroxy-1-(2'-hydroxyethyl)-2-methylpyrid-4-one or a salt thereof.*

*50. The pharmaceutical composition according to claim 8, in which the 3-hydroxypyridone is 3-hydroxy-1-(3'-hydroxypropyl)-2-methylpyrid-4-one or a salt thereof.*

*51. The pharmaceutical composition according to claim 9, in which the 3-hydroxypyridone is 3-hydroxy-1-(2'-hydroxyethyl)-2-methylpyrid-4-one or a salt thereof.*

*52. The compound according to claim 19, which is a 3-hydroxypyrid-4-one.*

*53. The compound according to claim 52, which is substituted at the 2-position.*

*54. The compound according to claim 19, in which the 3-hydroxypyridone is 3-hydroxy-1-(3'-hydroxypropyl)-2-methylpyrid-4-one or a salt thereof.*

*55. The compound according to claim 52, which is an N-substituted 2-alkyl-3-hydroxypyrid-4-one, 6-alkyl-3-hydroxypyrid-4-one or 2,6-dialkyl-3-hydroxypyrid-4-one wherein the alkyl group is methyl, ethyl, propyl or isopropyl.*

*56. The compound according to claim 19, in which the hydrogen atom attached to the nitrogen atom is replaced by a group —$(CH_2)_mOH$ wherein m is an integer of 2 to 4.*

*57. The compound according to claim 52, in which the nitrogen atom of the 3-hydroxypyrid-4-one is substituted by a group —$(CH_2)_mOH$ wherein m is an integer of 2 to 4, and the ring carbon atoms are either unsubstituted or the ring carbon atom at the 2-position is substituted by a methyl or ethyl group.*

*58. The compound according to claim 19, in which the hydrogen atom attached to the nitrogen atom is replaced by a $C_1$–$C_6$ aliphatic hydrocarbon group substituted by a formyloxy, ($C_1$–$C_4$ alkyl)-carbonyloxy, ($C_1$–$C_4$ alkyl)-oxycarbonyl, ($C_1$–$C_4$ alkyl)-sulphonyloxy or ($C_1$–$C_4$ alkyl)-oxysulphonyl group.*

* * * * *